(12) United States Patent
Batchelor et al.

(10) Patent No.: US 7,875,261 B2
(45) Date of Patent: Jan. 25, 2011

(54) FLUORINATED RESORUFIN COMPOUNDS AND THEIR APPLICATION

(75) Inventors: Robert Batchelor, Eugene, OR (US); Yue Ge, Cary, NC (US); Iain Johnson, Eugene, OR (US); Wai-Yee Leung, San Ramon, CA (US); Jixiang Liu, Eugene, OR (US); Brian Patch, Eugene, OR (US); Peter Smalley, Seattle, WA (US); Thomas Steinberg, Eugene, OR (US); Kyle Gee, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/015,476

(22) Filed: Jan. 16, 2008

(65) Prior Publication Data
US 2008/0113341 A1 May 15, 2008

Related U.S. Application Data

(62) Division of application No. 10/980,139, filed on Nov. 1, 2004, now Pat. No. 7,432,372.

(60) Provisional application No. 60/516,244, filed on Oct. 31, 2003.

(51) Int. Cl.
*A61B 10/00* (2006.01)
*A61B 5/00* (2006.01)

(52) U.S. Cl. .............. 424/9.6; 424/1.11; 424/1.65; 424/9.1; 206/223; 206/569; 544/101

(58) Field of Classification Search ......... 424/1.11, 424/1.65, 9.1, 9.2, 9.6, 1.81, 1.85, 1.89, 9.3, 424/9.4, 9.5, 9.7, 9.8; 544/63, 99, 101; 206/223, 206/569, 570; 435/5; 423/582, 584; 562/1; 252/186.22; 558/91
See application file for complete search history.

(56) References Cited

U.S. PATENT DOCUMENTS

| | | | |
|---|---|---|---|
| 4,384,042 A | 5/1983 | Miike et al. | |
| 4,420,568 A | 12/1983 | Wang et al. | |
| 4,510,251 A | 4/1985 | Kirkemo et al. | |
| 4,711,955 A | 12/1987 | Ward et al. | |
| 4,719,097 A | 1/1988 | Muhlegger et al. | |
| 4,737,466 A | 4/1988 | Klein et al. | |
| 4,954,630 A | 9/1990 | Klein et al. | |
| 4,997,928 A | 3/1991 | Hobbs | |
| 5,047,519 A | 9/1991 | Hobbs, et al. | |
| 5,049,673 A | 9/1991 | Tsien et al. | |
| 5,171,534 A | 12/1992 | Smith et al. | |
| 5,208,148 A | 5/1993 | Haugland et al. | |
| 5,304,645 A | 4/1994 | Klein et al. | |
| 5,332,666 A | 7/1994 | Prober et al. | |
| 5,352,803 A | 10/1994 | Mattingly | |
| 5,362,628 A | 11/1994 | Haugland et al. | |
| 5,405,975 A | 4/1995 | Kuhn et al. | |
| 5,453,517 A | 9/1995 | Kuhn et al. | |
| 5,459,268 A | 10/1995 | Haugland et al. | |
| 5,573,904 A | 11/1996 | Mattingly | |
| 5,576,424 A | 11/1996 | Mao et al. | |
| 5,648,270 A | 7/1997 | Kuhn et al. | |
| 5,686,261 A | 11/1997 | Zhang et al. | |
| 5,714,327 A | 2/1998 | Houthoff et al. | |
| 6,972,339 B2 * | 12/2005 | Lukhtanov et al. | ......... 558/91 |
| 7,432,372 B2 * | 10/2008 | Batchelor et al. | ......... 544/99 |

FOREIGN PATENT DOCUMENTS

| | | |
|---|---|---|
| EP | 0115394 | 8/1984 |
| EP | 0138481 | 6/1991 |
| GB | 2360846 | 10/2001 |
| WO | WO-2003/023357 | 3/2003 |
| WO | WO-03023357 | 3/2003 |
| WO | WO-05042504 | 5/2005 |

OTHER PUBLICATIONS

U.S. Appl. No. 10/980,139, "Final Rejection mailed Jul. 16, 2007".
U.S. Appl. No. 10/980,139, "Non-Final Rejection, mailed Jan. 29, 2008".
U.S. Appl. No. 10/980,139, "Non-Final Rejection, mailed Mar. 2, 2007".
U.S. Appl. No. 10/980,139, "Notice of Allowance, mailed May 30, 2008".
U.S. Appl. No. 10/980,139, "Response to Jan. 29, 2008 Non-Final Office Action, filed Mar. 28, 2008".
U.S. Appl. No. 10/980,139, "Response to Mar. 2, 2007 Non-Final Rejection, filed Jun. 28, 2007".
U.S. Appl. No. 10/980,139, "Response to Jul. 16, 2007 Final Rejection, filed Jan. 16, 2008".
U.S. Appl. No. 10/980,139, "Response to Jan. 23, 2007 Restriction Requirement filed Feb. 23, 2007".
U.S. Appl. No. 10/980,139, "Restriction Requirement mailed Jan. 23, 2007".
U.S. Appl. No. 10/980,139, "Supplemental Response or Amendment filed Jan. 24, 2008".
Bouizar, Z. et al., "Purification and Characterization of Calcitonin Receptors in Rat Kidney Membranes by Covalent Cross-Linking Techniques.", *Eur J Biochem* vol. 155(1) 1986, pp. 141-147.

(Continued)

*Primary Examiner*—D L Jones
(74) *Attorney, Agent, or Firm*—Life Technologies Corporation; James K. Blodgett

(57) ABSTRACT

The invention provides novel fluorinated resorufin compounds that are of use in a variety of assay formats. Also provided are methods of using the compounds and kits that include a compound of the invention and instructions detailing the use of the compound in one or more assay formats.

43 Claims, 10 Drawing Sheets

OTHER PUBLICATIONS

Browning, Jeffrey et al., "Studies on the Differing Effects of the Tumor Necrosis Factor and Lymphotoxin on the Growth of Several Human Tumor Lines", *The Journal of Immunology* vol. 143, No. 6 1989, pp. 1859-1867.

Database Beilstein 1999, "Databased Accession No. 8003161 (BRN) 7-(diethylamino)-1, 2-difluoro-phenoxazin-3-one &", *Russian Journal of Physical Chemistry* vol. 72, No. 2 1998, 272-276.

Database Caplus Chemical, "Abstracts Service, Columbus, Ohio US; 2002", *Database Accession No. 2002:257217 RN 204519-58-4, 439869-32-6& Materials Research Society Symposium Proceedings* vol. 677 2001, AA& 4 1 - AA7 4 6.

Database Caplus Chemical, "Chemical Abstracts Service", Columbus, Ohio US; 1982, Database Accession No. 1982:20048 RN 80287-45-2 & lzvestiya Sibirskogo Otdeleniya Akedemii Nauk SSSR, SeriyaSome Reactions of 10-Phenyloctafluorophenothiazine and its Oxide96:20048 5: 1981, 125-129.

EP04810240.4, "European Office Action, mailed Mar. 2, 2010".

EP04810240.4, "European Office Action, mailed Dec. 3, 2208".

EP04810240.4, "Response to Dec. 3, 2008 European Office action filed on Jun. 10, 2009.".

Furniss, Brian S. et al., "Resolution of Racemates", *Vogel's Textbook of Practical Organic Chemistry* Fifth Ed, Longman Group UK Ltd., Essex 1989, 809-823.

Gerasimova, T. N. et al., "Synthesis of Fluorinated 7-Diethylaminophenoxazin-3-ones and 9-Diethylamino-5H-Benzo[a]Phenoxazine5-Ones", *Russ. Journal of Org. Chem* vol. 33 1997, 735-739.

Haugland, Rosaria P., "Ch 22: Coupling of monoclonal antibodies with fluorophores", *Methods in Molecular Biology* vol. 45: Monoclonal Antibody Protocols 1995, 205-221.

Heller, A., "Electrical Wiring of Redox Enzymes", *Acc. Chem. Res.* vol. 23, No. 5 1990, 128-134.

Jung, S. M. et al., "Crosslinking of Platelet Glycoprotein lb by N-Succinimidyl (4-azidophenyldithio) Propionate and 3, 3'-dithiobis (Sulfosuccinimidyl Promionate)", *Biochimica et Biophysica Acta* vol. 761 1983, pp. 152-162.

Park, Linda S. et al., "Characterization of the Cell Surface Receptor for a Multi-Lineage Colony-Stimulating Factor (CSF-2alpha)*", *The Journal of Biological Chemistry* vol. 261, No. 1 1986, pp. 205-210.

PCT/US04/36546, "International Report on Patentability, mailed May 1, 2006".

PCT/US04/36546, "International Search Report", Mar. 31, 2005.

PCT/US04/36546, "PCT Written Opinion of the International Searching Authority, mailed Apr. 30, 2006".

Sandler, Stanley R. et al., *Organic Functional Group Preparations* vol. 3, New York: Academic Press 1972, 5-7.

Zarling, David A. et al., "Mapping of Lymphocyte Surface Polypeptide Antigens by Chemical Cross-Linking with BSOCOES", *The Journal of Immunology* vol. 124, No. 2 1980, pp. 913-920.

* cited by examiner

FLUORINATED RESORUFIN COMPOUNDS AND THEIR APPLICATION

CROSS-REFERENCE TO RELATED APPLICATIONS

This application is a divisional application of U.S. Ser. No. 10/980,139, filed Nov. 1, 2004, which application claims priority of U.S. Ser. No. 60/516,244, filed Oct. 31, 2003, which disclosures are herein incorporated by reference.

FIELD OF THE INVENTION

The present invention relates to novel fluorogenic compounds that have utility in detecting reactive oxygen species, e.g., hydrogen peroxide. The invention is of use in a variety of fields including immunology, diagnostics, molecular biology and fluorescence based assays.

BACKGROUND OF THE INVENTION

The study and detection of enzyme activity serve a wide range of purposes both in research laboratories and in clinical assays. Enzyme activity is monitored, for example, in determining physiological functions in patients during routine checkups or diagnostic procedures in general, in monitoring the exposure of workers and others to potentially harmful chemicals such as toxic or carcinogenic pesticides or inorganic materials in the atmosphere, soil, or drinking water, in determining the effectiveness of pharmaceuticals on disease states or conditions, in screening new compounds for biological activity as either promoters or inhibitors of particular enzymes, in monitoring gene and transgene expression, and in performing immunological and other laboratory assays such as enzyme-linked immunosorbent assays (ELISAs) and Western blots.

Optical methods of detection, such as fluorescence emission, UV absorptivity, and colorimetry are convenient and highly effective for detecting, monitoring, and measuring enzyme activity, since methods such as these can generate either qualitative or quantitative information and detection can be achieved either by direct visual observation or by instrumentation. Optically detectable reporters, i.e., synthetic or substitute substrates that are added to a sample and that display a measurable increase or other difference in optical detectability upon action of the enzyme, are therefore particularly useful. Examples of optical reporters that are currently known are 4-nitrophenol, α-naphthol, β-naphthol, resorufin and substituted resorufins, nitranilide, 5-bromo-4-chloro-3-indole, coumarin, xanthene and umbelliferone derivatives. The degree of change and hence the effectiveness of optical detection reporters depend on any of several factors, depending on the detection method for which they are used. Some of these factors are, a high extinction coefficient for reporters that are detectable by light absorptivity (particularly a large increase from substrate to product), a large change in the wavelength at which maximum absorptivity occurs (particularly a large substrate-to-product red shift), a substrate-to-product increase in the Stokes' shift for fluorescent reporters, and the chemical stability of the reporter.

With the advent of nanotechnology, there is an increased ability to perform numerous chemical and physical operations with very small volumes. This opportunity comes with the requirement that determinations have enhanced sensitivity to detect the few molecules that are present to provide the detectable signal. Part of the increased sensitivity may come from more sensitive detectors, but these are usually more expensive and are not readily available in most laboratories. An alternative is the provision of assays that rely on readily detectable labels. The assays may also be formatted to use compounds that are readily accepted by an enzyme as a substrate and efficiently convert a fluorogenic substrate to a fluorescent label.

Due to their reliable oxidation/reduction chemistry, resorufins are attractive fluorogenic substrates for use in assays to detect reactive oxygen species, e.g., peroxides, or enzymes that generate such species, e.g., peroxidases. Many resorufins are known in the art. For example, Miike et al. (U.S. Pat. Nos. 4,384,042; and 4,954,630) disclose the use of resorufins to detect hydrogen peroxide. Klein et al. (U.S. Pat. No. 5,304,645) discuss the preparation and use of a series of reactive resorufin derivatives and their conjugation to species such as ligands, haptens, antigens, antibodies and the like. Mühlegger et al. (U.S. Pat. No. 4,719,097) set forth resorufin phosphates for determining the activity of phosphatases. None of the cited references discloses a fluorinated resorufin analogue such as those of the present invention. Furthermore, until the present invention, the safe and reliable preparation of fluorinated resorufin derivatives was not known in the art.

SUMMARY OF THE INVENTION

It has now been discovered that fluorinated resorufins can be safely and reliably prepared. The fluorinated derivatives have improved fluorescent properties relative to non-fluorinated resorufin species. For example, the fluorescence of fluorinated resorufins is much more stable in high concentration of peroxide than the non-fluorinated resorufins. Due to its lower pKa, fluorination of the phenoxazine ring system of the resorufin markedly enhances the fluorescence intensity of the corresponding resorufin. The fluorinated resorufins are also more photostable under prolonged irradiation than the non-fluorinated analogues.

Thus, in a first aspect, the present invention provides a compound having the general formula:

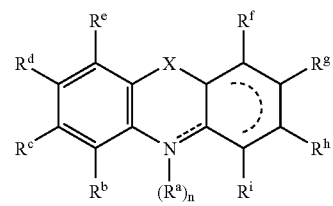

in which the symbol $R^a$ represents H, substituted or unsubstituted alkyl, substituted or unsubstituted aryl, O, and $C(X^a)R^{a1}$, in which $X^a$ represents O, S or NH and $R^{a1}$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, $OR^{a2}$ and $NR^{a3}R^{a4}$. The symbols $R^{a2}$, $R^{a3}$ and $R^{a4}$ independently represent moieties such as H, substituted or unsubstituted alkyl, substituted or unsubstituted heteroalkyl, substituted or unsubstituted heteroaryl and substituted or unsubstituted heterocycloalkyl. The index "n" represents either 0 or 1. $R^b$, $R^c$, $R^e$, $R^f$, $R^h$ and $R^i$ are members that are independently selected from the genus of aryl substituents, including species such as H, OH, sulfo, nitro, carboxyl, carboxylate esters, halogen, substituted or unsubstituted alkyl, substituted or unsubstituted heteroalkyl (e.g., alkoxy, alkylthio, aminoalkyl, etc.), substituted or unsubstituted aryl, substituted or unsubstituted heteroaryl, substituted or unsubstituted heterocycloalkyl and a reactive group. At least one of $R^b$, $R^c$, $R^e$, $R^f$, $R^h$ and $R^i$ is fluorine.

The symbol $R^d$ represents $OR^{d1}$ or $NR^{d1}R^{d2}$. $R^{d1}$ and $R^{d2}$ are members independently selected from H, substituted or unsubstituted alkyl, substituted or unsubstituted heteroalkyl, substituted or unsubstituted heteroaryl, substituted or unsubstituted heterocycloalkyl, substituted or unsubstituted acyl, and a reactive group. $R^g$ represents $OR^{g1}$, $NR^{g1}R^{g2}$ or (=O). The identities of $R^{g1}$ and $R^{g2}$ are the same as those set forth above for $R^{d1}$ and $R^{d2}$.

The invention also provides methods for using the fluorinated compounds to assay samples for the presence of a reactive oxygen species, such as peroxide, for detection of a specific analyte and for measuring metabolic activity in a cell. In an exemplary embodiment, the assay is of use to detect and/or quantitate a reactive oxygen species or an enzyme that generates a reactive oxygen species in the sample.

In still a further aspect, the invention provides kits that include a compound of the invention and directions for making use of the compound.

Other aspects, objects and advantages of the present invention will be apparent from the detailed description that follows.

DETAILED DESCRIPTION OF THE INVENTION

Introduction

Figure 1:
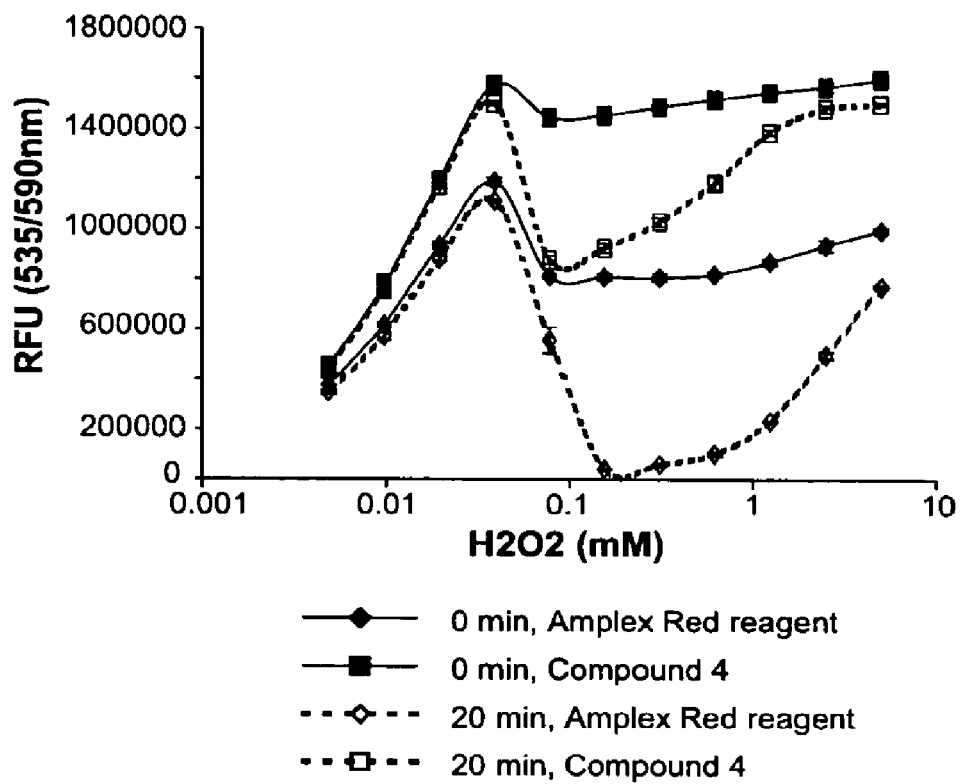
FIG. 1: is a plot of the fluorescence of Amplex Red reagent vs. Compound 4 in a high hydrogen peroxide titration in a horseradish peroxidase assay. Initially the fluorescence intensity of both dyes is relatively stable in the presence of high concentrations of $H_2O_2$, but after twenty minutes of incubation, there is a biphasic mode to the dilution series, whereby the fluorescence has a peak at ~40 µM $H_2O_2$, then quickly drops at 80-160 µM $H_2O_2$ rising slowly at higher concentrations.

There is a continuous and expanding need for rapid, highly specific methods of detecting and quantifying chemical, biochemical and biological analytes in research and diagnostic mixtures. Of particular value are methods for measuring small quantities of nucleic acids, peptides (e.g., enzymes), pharmaceuticals, metabolites, microorganisms and other materials of diagnostic value. Examples of such materials include narcotics and poisons, drugs administered for therapeutic purposes, hormones, pathogenic microorganisms and viruses, antibodies, and enzymes and nucleic acids, particularly those implicated in disease states.

One method of detecting an analyte relies on directly or indirectly labeling the analyte or other component of the analysis mixture with a fluorescent species. Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling.

As discussed herein, the present invention provides a new class of fluorinated fluorescent probes that are of use in a variety of analytical techniques.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a fluorogenic compound" includes a plurality of compounds and reference to "an enzyme" includes a plurality of enzymes and the like.

Unless defined otherwise, all technical and scientific terms used herein have the same meaning as commonly understood by one of ordinary skill in the art to which this invention is related. The following terms are defined for purposes of the invention as described herein.

The symbol , whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s)

are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "buffer" as used herein refers to a system that acts to minimize the change in acidity or basicity of the solution against addition or depletion of chemical substances.

The term "carbonyl" as used herein refers to the functional group —(C=O)—. However, it will be appreciated that this group may be replaced with other well-known groups that have similar electronic and/or steric character, such as thiocarbonyl (—(C=S)—); sulfinyl (—S(O)—); sulfonyl (—SO$_2$)—), phosphonyl (—PO$_2$—).

The term "Carboxyalkyl" as used herein refers to a group having the general formula —(CH$_2$)$_n$COOH wherein n is 1-18.

The term "carrier molecule" as used herein refers to a fluorogenic, fluorescent or calorimetric compound of the present invention that is covalently bonded to a biological or a non-biological component. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "enzymatic peroxide producing system" used herein refers to a system comprising an enzyme and an appropriate substrate wherein at least one of the resulting products is peroxide.

The term "enzyme" as used herein refers to a peptide with catalytic activity.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "kit" as used refers to a packaged set of related components, typically one or more compounds or compositions.

The term "Linker" or "L", as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

As used herein "peroxidase" refers to an enzyme that catalyzes the oxidation of a molecule by a peroxide. This includes all enzymes that contain peroxidase activity, including, but not limited to, cyclooxygenase, horseradish peroxidase and myeloperoxidase.

As used herein "peroxide" refers to a molecule that includes the —O—O— moiety.

The term "protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage resulting in a fluorescent or fluorogenic labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "salt thereof," as used herein includes salts of the agents of the invention and their conjugates, which are preferably prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium, or a similar salt. When compounds of the present invention contain relatively basic functionalities, acid addition salts can be obtained by contacting the neutral form of such compounds with a sufficient amount of the desired acid, either neat or in a suitable inert solvent. Examples of addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The term "sample" as used herein refers to any material that may contain a peroxide. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. Solid supports may be present in a variety of forms, including a chip, wafer or well, onto which an individual, or more than one compound, of the invention is bound such as a polymeric bead or particle.

The term "sulfoalkyl," as used herein refers to a group having the general formula —$(CH_2)_nSO_3$ wherein n is 1-18.

The term "targeting group" as used herein refers to a moiety that is: (1) able to actively direct the entity to which it is attached (e.g., a fluorogenic moiety) to a target region, e.g., a cell; or (2) is preferentially passively absorbed by or entrained within a target region. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly(ethers), dendrimers, poly(amino acids) and so forth.

The Compounds

The present invention provides both fluorogenic and fluorescent compounds based on a ring system according to Formula I:

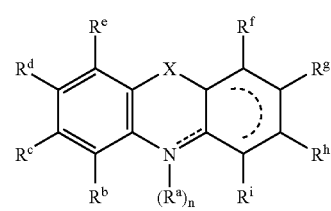

in which the symbol $R^a$ represents H, substituted or unsubstituted alkyl, substituted or unsubstituted aryl, O, and $C(X^a)R^{a1}$, in which $X^a$ represents O, S or NH and $R^{a1}$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted acyl, $OR^{a2}$ and $NR^{a3}R^{a4}$. The symbols $R^{a2}$, $R^{a3}$ and $R^{a4}$ independently represent moieties such as hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, a reactive group, substituted reactive group, carrier molecule, substituted carrier molecule, solid support or substituted solid support. Alternatively, a member independently selected from $R^{d1}$ in combination with $R^{d2}$; $R^{d1}$ in combination with $R^c$; $R^{d1}$ in combination with $R^e$; $R^{d1}$ in combination with $R^f$; and $R^{d2}$ in combination with $R^i$ together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl.

The index "n" represents either 0 or 1.

$R^b$, $R^c$, $R^e$, $R^f$, $R^h$ and $R^i$ are members that are independently selected from the genus of aryl substituents, including species such as H, OH, sulfo, nitro, carboxyl, carboxylate esters, halogen, substituted or unsubstituted alkyl, substituted or unsubstituted heteroalkyl (e.g., alkoxy, alkylthio, aminoalkyl, etc.), substituted or unsubstituted aryl, substituted or unsubstituted heteroaryl, substituted or unsubstituted heterocycloalkyl, a reactive group, substituted reactive group, a carrier molecule, substituted carrier molecule, a solid support or substituted solid support. Alternatively, a member independently selected from $R^b$ in combination with $R^c$; and $R^h$ in combination with $R^i$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl. At least one of $R^b$, $R^c$, $R^e$, $R^f$, $R^h$ and $R^i$ is fluorine.

The symbol $R^d$ represents $OR^{d1}$ or $NR^{d1}R^{d2}$. The identities of $R^{d1}$ and $R^{d2}$ are the same as those set forth for $R^{a1}$, $R^{a3}$ and $R^{a4}$. $R^g$ represents $OR^{g1}$, $NR^{g1}R^{g2}$ or (=O). The identities of $R^{g1}$ and $R^{g2}$ are the same as those set forth above for $R^{d1}$ and $R^{d2}$.

The dashed lines in the formula represent double bonds that are either present or absent as required to satisfy the rules of valency. Thus, the formula above includes the following exemplary substructures:

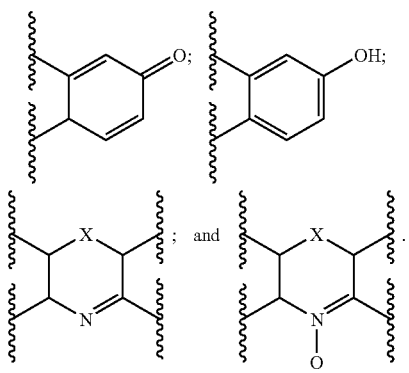

In an exemplary embodiment, the invention provides a compound according to Formula I that has the structure:

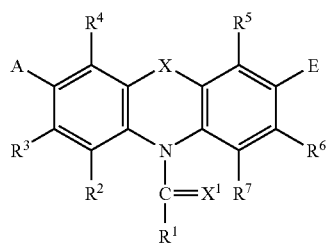

in which the symbols A and E independently represent a member selected from $OR^8$ and $NR^9R^{10}$. $R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, a reactive group, substituted reactive group, carrier molecule, substituted carrier molecule, solid support or substituted solid support. The groups $R^9$ and $R^{10}$ are independently hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, a reactive group, substituted reactive group, carrier molecule, substituted carrier molecule, solid support or substituted solid support.

Selected substituents, together with the ring system atoms to which they are attached, are optionally joined to form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl. Exemplary substituents that can be cyclized in this manner include $R^9$ in combination with $R^{10}$; $R^9$ in combination with $R^3$; $R^9$ in combination with $R^6$; $R^{10}$ in combination with $R^4$; and $R^{10}$ in combination with $R^5$. X is either oxygen or sulfur.

$R^1$ is a substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$. $X^1$ is either oxygen or sulfur.

The symbols $R^2$, $R^3$, $R^4$, $R^5$, $R^6$ and $R^7$ independently represent hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, a reactive group, substituted reactive group, a carrier molecule, substituted carrier molecule, a solid support or substituted solid support. In an exemplary embodiment, at least one of $R^2$, $R^3$, $R^4$, $R^5$, $R^6$ and $R^7$ is fluorine.

In one embodiment, the present compounds are according to the formula:

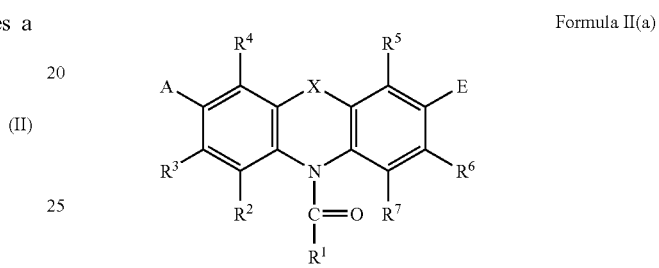

Formula II(a)

wherein $R^1$ is a substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$. The identities of $R^2$, $R^3$, $R^4$, $R^5$, $R^6$, $R^7$, X, A and E are the same as those set forth above.

In an exemplary embodiment $R^1$ is an alkyl, typically methyl, A and E are both $OR^8$, wherein $R^8$ is typically an alkyl or hydrogen and wherein at least one of $R^2$, $R^3$, $R^4$, $R^5$, $R^6$ or $R^7$ is fluorine.

Thus is one aspect, the present compounds are according to the formula:

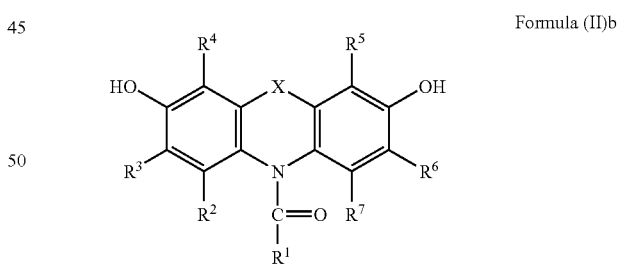

Formula (II)b

In one aspect, at least one of $R^3$, $R^4$, $R^5$, and $R^6$ is fluorine. In another aspect $R^3$ and $R^6$ are each fluorine. In a further aspect, $R^3$ and $R^6$ are each fluorine and $R^2$, $R^4$, $R^5$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl. Typically $R^2$, $R^4$, $R^5$ and $R^7$ are each hydrogen.

In another aspect, $R^4$ and $R^5$ are each fluorine wherein $R^2$, $R^3$, $R^6$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl. In a further aspect, $R^2$, $R^3$, $R^6$ and $R^7$ are each hydrogen.

In yet another aspect, $R^3$, $R^4$, $R^5$ and $R^6$ are each fluorine wherein $R^2$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl.

In another exemplary embodiment, A and E are each $NR^9R^{10}$ and $R^9$ and $R^{10}$ are independently hydrogen, substituted alkyl or unsubstituted alkyl. Typically $R^9$ and $R^{10}$ are each hydrogen.

Exemplary compounds according to Formula II(b) of the invention include those having the formulae:

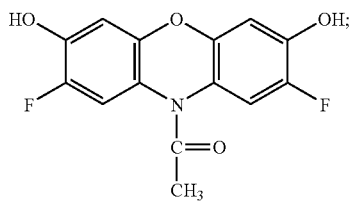

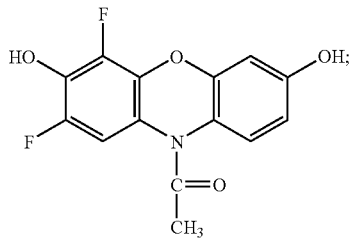

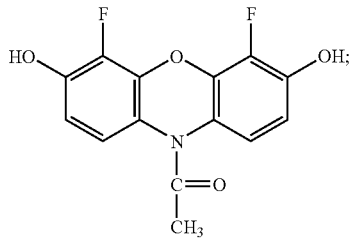

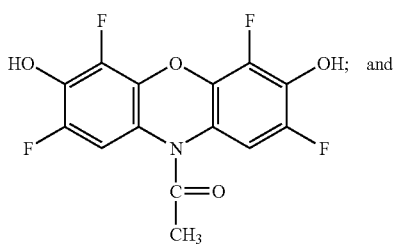

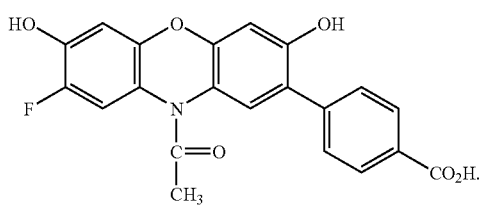

In certain embodiments, the compounds of the present invention have the formula:

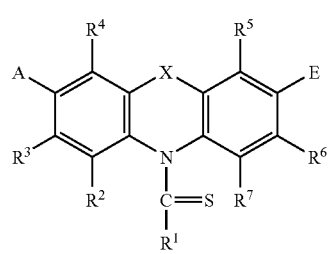

Formula (II)c

In this instance $R^1$ is a substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$. The identities of $R^2$, $R^3$, $R^4$, $R^5$, $R^6$, $R^7$, X, A and E are the same as those set forth above.

In another exemplary embodiment, the invention provides compounds according to Formula III:

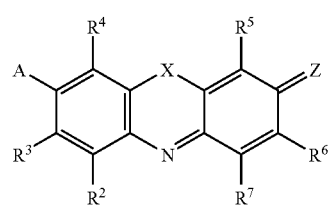

(III)

wherein A is $OR^8$ or $NR^9R^{10}$, Z is either oxygen (O) or a quaternized amine, $N^+R^9R^{10}$. At least one of $R^2$, $R^3$, $R^4$, $R^5$, $R^6$ and $R^7$ is fluorine. The identities of $R^2$, $R^3$, $R^4$, $R^5$, $R^6$ and $R^7$ are the same as those set above.

The compounds according to Formula (III) are inherently fluorescent and are generally referred to as oxazine dyes or thiazine dyes. They can be used with the many methods of the present invention, including as spectrally matched controls for the fluorogenic compounds according to formula II. It is understood that the fluorogenic compounds according to Formula II (hydroxyl derivative) are converted into corresponding Formula III (ketone derivative) compounds after reaction with peroxide.

In an exemplary embodiment A is $OR^8$ and Z is O, wherein $R^3$ is typically an alkyl or hydrogen and wherein at least one of $R^2$, $R^3$, $R^4$, $R^5$, $R^6$ or $R^7$ is fluorine.

Thus is one aspect, the present compounds are according to the formula:

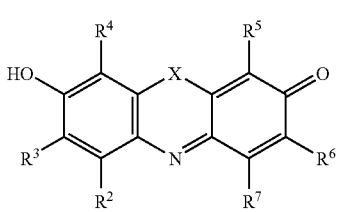

Formula III(a)

In one aspect, at least one of $R^3$, $R^4$, $R^5$, and $R^6$ is fluorine. In another aspect $R^3$ and $R^6$ are each fluorine. In a further aspect, $R^3$ and $R^6$ are each fluorine and $R^2$, $R^4$, $R^5$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl. Typically $R^2$, $R^4$, $R^5$ and $R^7$ are each hydrogen.

In another aspect, $R^4$ and $R^5$ are each fluorine wherein $R^2$, $R^3$, $R^6$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl. In a further aspect, $R^2$, $R^3$, $R^6$ and $R^7$ are each hydrogen.

In yet another aspect, $R^3$, $R^4$, $R^5$ and $R^6$ are each fluorine wherein $R^2$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl.

In another exemplary embodiment, A is $NR^9R^{10}$ and Z is $N^+R^9R^{10}$ and $R^9$ and $R^{10}$ are independently hydrogen, substituted alkyl or unsubstituted alkyl. Typically $R^9$ and $R^{10}$ are each hydrogen.

In an exemplary embodiment, at least one of $R^2$, $R^3$, $R^4$, $R^5$, $R^6$ and $R^7$, which is not a fluoro, is a reactive group, a carrier molecule or solid support. The atoms and groups represented by symbols in Formula III other than those discussed explicitly above are substantially identical to those described for the compounds of Formula II.

In still a further exemplary embodiment, the compounds of the invention have a structure according to Formula IV:

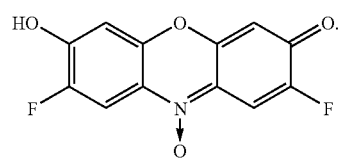

(IV)

in which the atoms and groups represented by the symbols in the formula are substantially identical to those described for the corresponding symbols of Formula III, provided that at least one of the R groups is fluorine. Compounds according to Formula (IV) are fluorogenic and as generally referred to as resazurin compounds.

In an exemplary embodiment A is $OR^8$ and Z is O, wherein $R^3$ is typically an alkyl or hydrogen and wherein at least one of $R^2$, $R^3$, $R^4$, $R^5$, $R^6$ or $R^7$ is fluorine.

In one aspect, at least one of $R^3$, $R^4$, $R^5$, and $R^6$ is fluorine. In another aspect $R^3$ and $R^6$ are each fluorine. In a further aspect, $R^3$ and $R^6$ are each fluorine and $R^2$, $R^4$, $R^5$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl. Typically $R^2$, $R^4$, $R^5$ and $R^7$ are each hydrogen.

In another aspect, $R^4$ and $R^5$ are each fluorine wherein $R^2$, $R^3$, $R^6$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl. In a further aspect, $R^2$, $R^3$, $R^6$ and $R^7$ are each hydrogen.

In yet another aspect, $R^3$, $R^4$, $R^5$ and $R^6$ are each fluorine wherein $R^2$ and $R^7$ are hydrogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, or unsubstituted heteroaryl.

In another exemplary embodiment, A is $NR^9R^{10}$ and Z is $N^+R^9R^{10}$ and $R^9$ and $R^{10}$ are independently hydrogen, substituted alkyl or unsubstituted alkyl. Typically $R^9$ and $R^{10}$ are each hydrogen.

An exemplary compound according to Formula IV is compound 32:

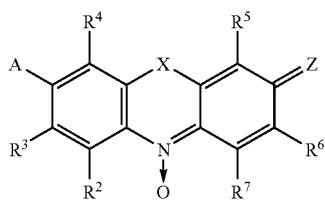

Synthesis

In an exemplary route, the compounds of the invention are prepared starting with a fluorinated resorcinol, which is nitrosated and condensed with another resorcinol. Prior to the present invention, it was not recognized that a nitrosofluororesorcinol could be prepared and condensed with a resorcinol partner to produce the fused ring system described herein. Thus, it is an aspect of the present invention to prepare fluorogenic and fluorescent compounds according to Formulae I-IV by a route according to Scheme 1. In Scheme I, the synthesis begins with the nitrosation of a selected resorcinol. The precursor resorcinol may be substituted at one or more of the 2-, 5-, or 6-position(s). In an exemplary synthetic route, the resulting 4-nitroso-resorcinol (a) is condensed in warm acid with a resorcinol (b) that may be substituted at the 2-, 4-, and/or 5-positions, but preferably not at the 6-position. The resulting resorufin (c) is reduced to the dihydro form (d). The secondary amine moiety in d is optionally acylated, affording e. At least one of $Y^a$, $Y^{a'}$, $Y^b$, $Y^{b'}$, $Y^c$, $Y^{c'}$, is fluorine.

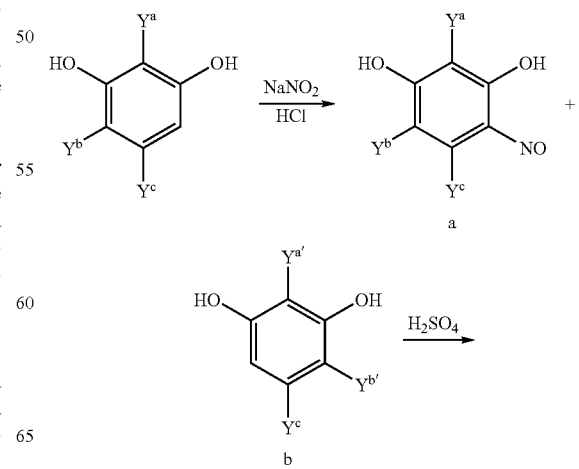

Scheme 1:

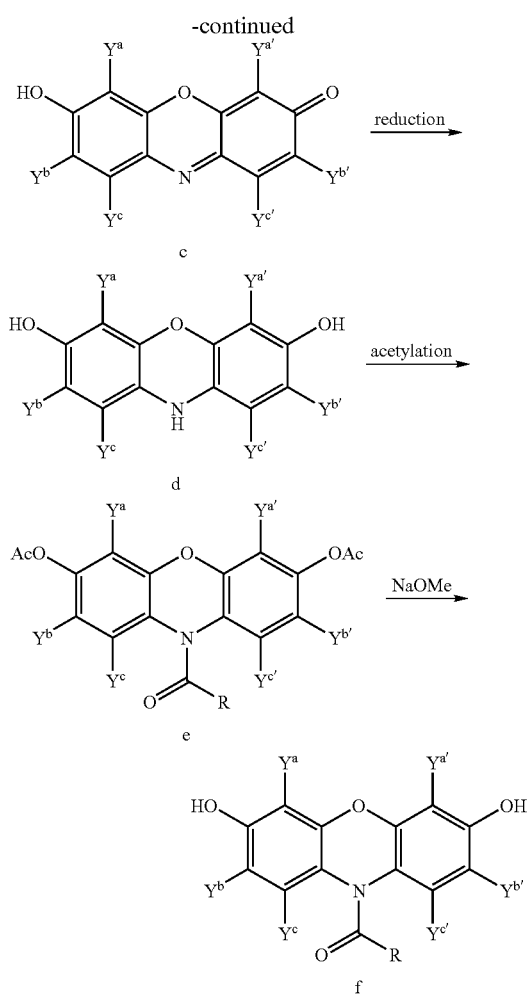

The reduced derivatives of fluorinated resorufin dyes are prepared by chemical reduction of the ketone moiety portion with stannous chloride in organic solvents. These dihydroxy-fluorinated compounds can serve as substrates for enzymes that take up electrons, or in the detection of chemical oxidizing agents, reactive oxygen species or nitric oxides.

Several other moieties are optionally present during these synthetic steps; they may either be protected with a protecting group or resistant to the steps required for synthesis of the fluorinated compound. Exemplary moieties include alkyl, carboxyalkyl, chloro, bromo, iodo, alkoxy and hydroxy. Hydroxy moieties may also be formed during cleavage of alkoxy groups present in the starting material.

The dihydroxyphenoxazine and phenoxazin-3-one versions of the dyes of the invention and their conjugates are generally freely interconvertible by chemical oxidation or reduction. Reagents useful for this reduction include borohydrides, aluminum hydrides, hydrogen in the presence of a hydrogenation catalyst, and dithionites. Choice of the reducing agent may depend on the ease of reduction of other reducible groups in the molecule.

Figure 2:
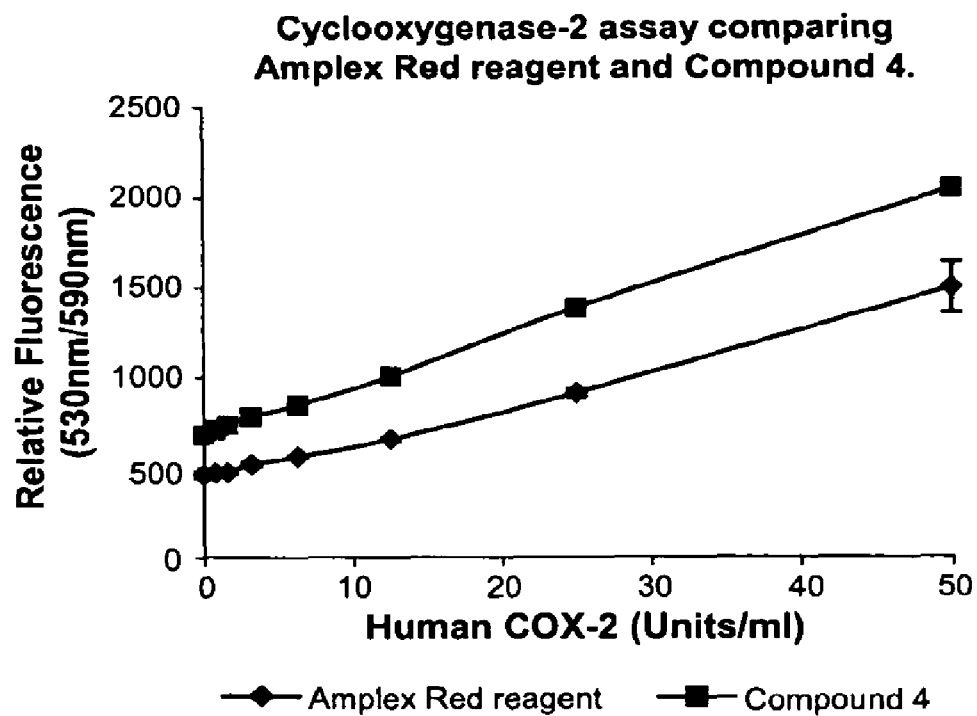
FIG. 2: is a plot of a cycloxygenase assay comparing the fluorescence of Amplex Red reagent with Compound 4. The plot shows that both dye reagents are oxidized to their fluorescent forms by COX-2. The dynamic range and sensitivity of both dyes is similar with Compound 4 demonstrating a greater fluorescent intensity signal. Error bars in the graph are one standard deviation from the mean of three measurements.
Figure 3:
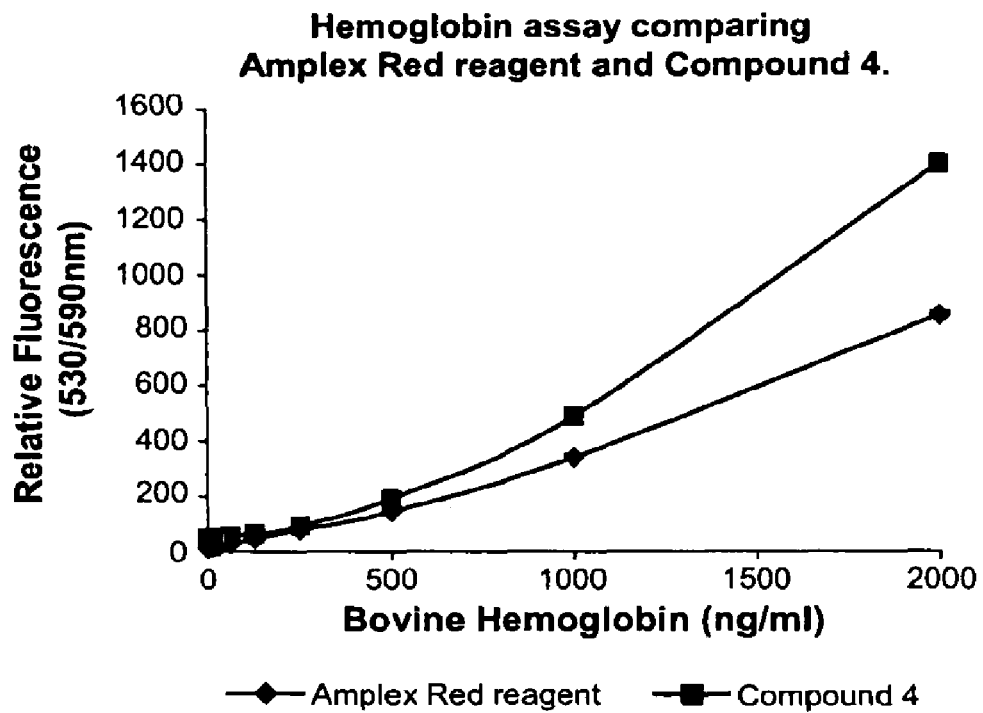
FIG. 3: is a plot of a hemoglobin assay comparing the fluorescence of Amplex Red reagent with Compound 4. The figure shows that both dye reagents are oxidized to their fluorescent forms by bovine hemoglobin. Although the dynamic range and sensitivity of both dyes is similar, Compound 4 is brighter. Error bars in the graph are one standard deviation from the mean of three measurements.

A wide variety of oxidizing agents mediate the oxidation of the dihydroxyphenoxazine, including molecular oxygen in the presence or absence of a catalyst, peroxide, nitric oxide, peroxynitrite, dichromate, triphenylcarbenium and chloranil. The dihydroxyphenoxazines are also oxidized by enzymatic action, including the action of horseradish peroxidase in combination with peroxides (Example 33; FIG. 1), by cyclooxygenase (Example 34; FIG. 2), hemoglobin (Example 35; FIG. 3) or solely by nitric oxide. This oxidation may occur in a cell, or in a cell-free solution.

Post-condensation modifications of the fluorinated keto- and dihydroxy-phenoxazines are similar to known methods of modifying their non-fluorinated analogues.

The compounds of the invention also exist in other enzyme substrate formats. For example, the fluorinated compounds can be derivatized at a phenolic hydroxyl with phosphate (to give phosphatase substrates), carboxylic acids (to give esterase substrates), alkylation with alkyl groups (to give dealkylase substrates) and carbohydrates to yield glycosidase substrates. Moreover, the invention provides compounds in which the ring system, or a substituent thereon, includes a lipophilic moiety, such as a long chain fatty acid or alcohol moiety, or a phospholipids.

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, and solid supports, comprise a linker that is used to covalently attach the substituents to any of the moieties of the present compounds. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. The linker may also be substituted to alter the physical properties of the reporter moiety or chelating moiety, such as spectral properties of the dye.

The linker typically incorporates 1-30 nonhydrogen atoms selected from the group consisting of C, N, O, S and P. The linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, and arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —(CH$_2$)$_d$(CONH(CH$_2$)$_e$)$_z$— or where d is an integer from 0-5, e is an integer from 1-5 and z is 0 or 1. In a further embodiment, the linker is or incorporates the formula —O—(CH$_2$)—. In yet another embodiment, the linker is or incorporates a phenylene or a 2-carboxy-substituted phenylene.

An important feature of the linker is to provide an adequate space between the carrier molecule, reactive group or solid support and the dye so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^b$, $R^c$, $R^{d1}$, $R^{d2}$, $R^e$, $R^f$, $R^h$, $R^i$, $R^2$, $R^3$, $R^4$, $R^5$, $R^6$, $R^7$, $R^8$, $R^9$, or $R^{10}$ comprises a reactive group. Preferably, at least one of $R^b$, $R^c$, $R^e$, $R^f$, $R^h$, $R^i$, $R^2$, $R^3$, $R^4$, $R^5$, $R^6$, or $R^7$ comprises a reactive group or is attached to a reactive group. Alternatively, if the present compound comprises a carrier molecule or solid support a reactive group may be covalently attached independently to those substituents, allowing for further conjugation to a another dye, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

The pro-reactive groups are synthesized during the formation of the monomer moieties and carrier molecule and solid support containing compounds to provide chemically reactive compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
| --- | --- | --- |
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$)sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or moretimes by electron withdrawing substituents such as nitro, fluoro, chloro, cyano, ortrifluoromethyl, or combinations thereof, used to form activated aryl esters; or a carboxylic acid activated by a carbodiimide to form an anhydride or mixed anhydride —OCOR$^a$ or —OCNR$^a$NHR$^b$, whereR$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In exemplary embodiment, at least one member selected from $R^b$, $R^c$, $R^{d1}$, $R^{d2}$, $R^e$, $R^f$, $R^h$, $R^i$, $R^2$, $R^3$, $R^4$, $R^5$, $R^6$, $R^7$, $R^8$, $R^9$, or $R^{10}$ comprises a carrier molecule. Preferably, at least one of $R^b$, $R^c$, $R^e$, $R^f$, $R^h$, $R^i$, $R^2$, $R^3$, $R^4$, $R^5$, $R^6$, or $R^7$ comprises a carrier molecule or is attached to a carrier molecule. Alternatively, if the present compound comprises a reactive group or solid support a reactive group may be covalently attached independently to those substituents, allowing for further conjugation to a reactive group, carrier molecule or solid support.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binging proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —CH$_2$OCOalkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., Am. J. Physiol., 256: C540 (1989); and pyridyl-based and phenanthroline metal ion chelators, as described in U.S. Pat. No. 5,648,270 to Kuhn et al. (1997).

Fluorescent conjugates of metal chelating moieties possess utility as indicators for the presence of a desired metal ion. While fluorescent ion-indicators are known in the art, the incorporation of the fluorinated fluorogenic and fluorescent compounds of the present invention imparts the highly advantageous properties of the instant fluorophores onto the resulting ion indicator.

The ion-sensing conjugates of the invention are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DMA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization In an exemplary embodiment, the present compounds of the invention are covalently bonded to a solid support. The solid support may be attached to the compound or through a reactive group, if present, or through a carrier molecule, if present. Even if a reactive group and/or a carrier molecule are present, the solid support may be attached through the A, L or B moiety.

In exemplary embodiment, at least one member selected from $R^b$, $R^c$, $R^{d1}$, $R^{d2}$, $R^e$, $R^f$, $R^h$, $R^i$, $R^2$, $R^3$, $R^4$, $R^5$, $R^6$, $R^7$, $R^8$, $R^9$, or $R^{10}$ comprises a solid support. Preferably, at least one of $R^b$, $R^c$, $R^e$, $R^f$, $R^h$, $R^i$, $R^2$, $R^3$, $R^4$, $R^5$, $R^6$, or $R^7$ comprises a solid support or is attached to a solid support. Alternatively, if the present compound comprises a carrier molecule or reactive group a solid support may be covalently attached independently to those substituents, allowing for further conjugation to a another dye, carrier molecule or solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

Conjugates of components (carrier molecules or solid supports), e.g., drugs, peptides, toxins, nucleotides, phospholipids and other organic molecules are prepared by organic synthesis methods using the reactive reporter molecules of the invention, are generally prepared by means well recognized in the art (Haugland, MOLECULAR PROBES HANDBOOK, supra, (2002)). Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of Peptide or Protein Conjugates Typically Comprises First Dissolving the Protein to be conjugated in aqueous buffer at about. 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in an aprotic solvent (usually DMSO or DMF) in an amount sufficient to give a suitable degree of labeling when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the reporter molecule or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Applications and Methods of Use

The present invention also provides methods of using the compounds described herein to detect peroxidase activity in a sample, directly or indirectly by the production of peroxide. The methods are illustrated by the use of the compound of the invention to detect an active oxygen species, e.g. those of skill in the art will appreciate that this focus is for clarity of illustration and does not limit the scope of the methods in which the compounds of the invention find use.

In another embodiment, the present invention provides methods of using the compounds described herein to detect an analyte in a sample or as a tracing or tracking reagent in a biological sample. Alternatively, the present compounds are also used to detect to monitor metabolic activity in a cell including cell vialability and proliferation.

In one embodiment, for the detection of peroxidase activity, the selected methods of the invention exploit the facile oxidation/reduction chemistry of the compounds of the invention, relying on the interconversion between a hydroxy derivative and the corresponding ketone as shown below:

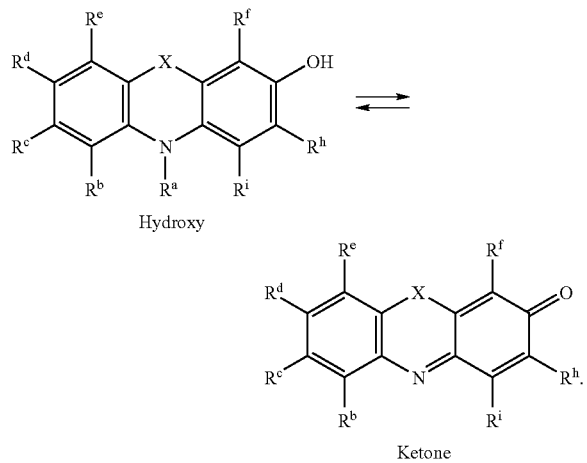

Thus, in a further aspect, there is provided a method for determining the presence or absence of peroxide in a sample. The method includes:
a) contacting the sample with a fluorogenic compound to prepare a labeled sample, wherein the fluorogenic compound is according to formula II;
b) incubating the labeled sample for a sufficient amount of time to prepare an incubated sample, wherein the peroxide reacts with the compound in the presence of a peroxidase to produce a fluorescent product;
c) illuminating the incubated sample with an appropriate wavelength to prepare an illuminated sample; and
d) observing the illuminated sample whereby the presence or absence of the peroxide in the sample is determined.

The peroxidase may be an enzyme such as horseradish peroxidase or an enzyme that has peroxidase activity, but which is not generally considered a peroxidase, such as cyclooxygenase. Typically, the peroxidase is horseradish peroxidase.

In certain embodiments, the peroxide detected is hydrogen peroxide, such as that produced by horseradish peroxidase. In another embodiment, the peroxide is not hydrogen peroxide, such as the transient peroxide produced by cyclooxygenase.

In another embodiment, the invention provides a modified version of the method set forth above for detecting peroxide in a sample. In the modified method, the peroxide is generated by an enzymatic reaction, e.g., the oxidation of a substrate by an oxidase. The compound of the invention is added to the assay mixture at any time prior to or during the generation of the peroxide. The reaction of the peroxide with the peroxidase can occur in the presence of the oxidase or other peroxide generating system. Thus, it is within the scope of the methods of the invention to react the peroxide with the peroxidase essentially simultaneously with the generation of the peroxide by the oxidase.

Exemplary enzymes of use in the methods of the invention include horseradish peroxidase as the required peroxidase; and oxidases such as glutamate oxidase, amine oxidase, choline oxidase, cholesterol oxidase, galactose oxidase, xanthine oxidase, uricase oxidase, pyruvate oxidase, glycerin-3-phosphate oxidase, acyl Co A oxidase, glycerol oxidase and glucose oxidase to generate peroxide.

As illustrated in FIG. 1, the compounds of the invention are of use to detect peroxide, e.g., hydrogen peroxide in a sample. The compounds of the invention provide enhanced fluorescent signal relative to the analogous non-fluorinated compound. Moreover, the compound of the invention provides a fluorescence signal that is more stable over a prolonged period in the presence of peroxide than is that of the corresponding non-fluorinated compound.

The compounds of the invention are also of use to detect the presence of an oxidase in a sample wherein the oxidase generates peroxide that is detected in the presence of peroxides by a fluorogenic compound of the present invention. As shown in FIG. 2, an exemplary compound of the invention and its non-fluorinated analogue are both oxidized to fluorescent species by the action of COX-2. The compound of the invention provides a greater fluorescence signal intensity than is observed for its non-fluorinated analogue.

In another example, a compound of the invention is utilized to detect hemoglobin in a sample. FIG. 3 shows that the fluorinated compound of the invention provides a fluorescent signal in the presence of hemoglobin that is enhanced relative to that observed for the non-fluorinated analogue.

In another example, a compound of the present invention is used to detect the activity of an acidic enzyme, phytase. This was an unexpected result and a clear advantage over known compounds for detecting peroxide in a sample, See, FIG. 10. This performance advantage of the present compounds is not confined to increased fluorescent signal (brightness) but also superior limit of detection as determined by Z-factor analysis, See Example 42. In the case of the phytase assay Compound 4 is shown to have superior resistance to bleaching due to over-oxidation, thus contributing to an extended dynamic range in comparison to Amplex Red reagent. This phenomenon was further tested where the activity of HRP was measured in a range of pH compared to Amplex Red Reagent, See FIGS. 6 and 9. The present fluorinated compounds demonstrate the ability to detect peroxide in a broader pH range than Amplex Red Reagent, providing for the ability of the present compounds to be used in acidic environments compared to the known Amplex Red reagent.

In another example, a compound of the present invention is used for the indirect detection of lipase activity. In this instance, lipase activity, in cells, breaks down triglycerides into free fatty acids and glycerol. In an assay format glycerol kinase and glycerol phosphate oxidase is added wherein the glycerol phosphorylated the glycerol and the glycerol oxidase oxidizes the phosphorylated glycerol producing $H_2O_2$. Thus with the addition of HRP the peroxidase is detected resulting in a correlation to the lipase activity of cells. This particular assay has diagnostic applications wherein the effect of drugs and diet can be accurately assessed for their affect on lipase activity, which plays a role in the degradation of unwanted triglycerides.

Figure 4:
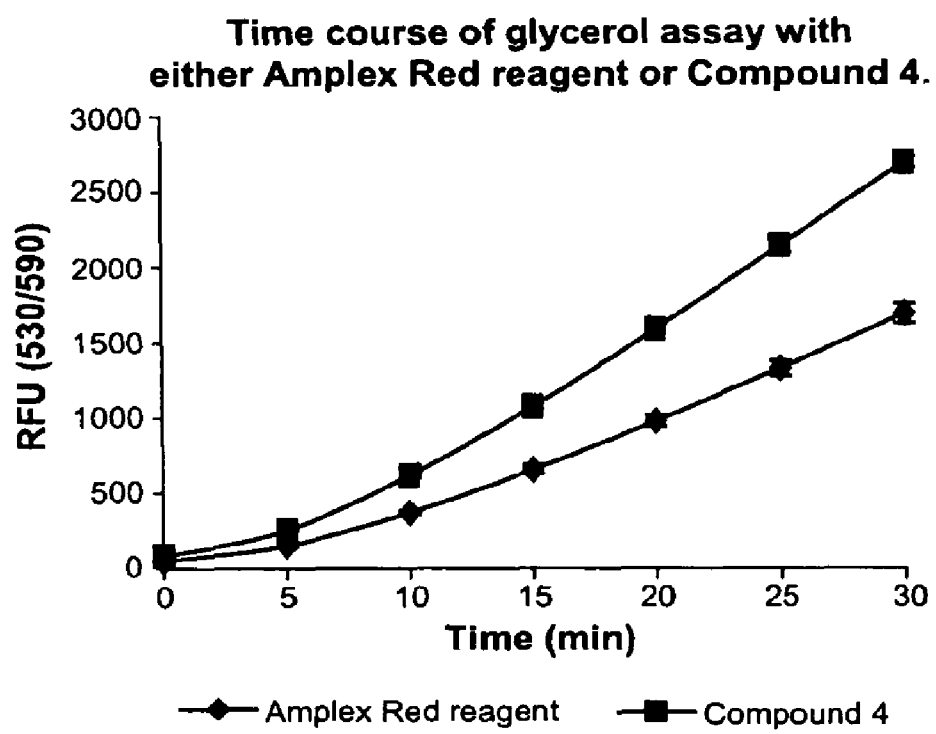
FIG. 4: is a plot showing the time course of a glycerol assay comparing the fluorescence of Amplex Red reagent with Compound 4. The figure shows that both dye reagents are oxidized to their fluorescent forms by bovine hemoglobin. Although the dynamic range and sensitivity of both dyes is similar, Compound 4 is brighter. Error bars in the graph are one standard deviation from the mean of three measurements.

FIG. 4 shows that the fluorinated compound of the invention provides a fluorescent signal that is enhanced relative to that observed for the non-fluorinated analogue. Alternatively, an assay is designed as a more direct measure of lipase activity, wherein triglycerides are used instead of glycerol along with triglyceride lipase, See Example 51.

In another embodiment, the peroxidase is covalently attached to a carrier molecule. In this instance, carrier molecules include, but are not limited to, an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus. In a further aspect, the carrier molecules is an antibody or fragment thereof, an avidin or streptavidin, a biotin, a blood component protein, a dextran, an antibody-binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

Thus, the present invention provides a modified method for determining the presence or absence of an analyte in a sample, wherein the method comprises:
  a) contacting the sample with a peroxidase enzyme covalently attached to a carrier molecule to prepare a contacted sample, wherein the carrier molecule directly or indirectly associates with the analyte;
  b) contacting the contacted sample with a fluorogenic compound to prepare a labeled sample, wherein the fluorogenic compound is according to formula II;
  c) incubating the labeled sample for a sufficient amount of time to prepare an incubated sample, wherein the peroxide reacts with the compound in the presence of a peroxidase to produce a fluorescent product;
  d) illuminating the incubated sample with an appropriate wavelength to prepare an illuminated sample; and
  e) observing the illuminated sample whereby the presence or absence of the analyte in the sample is determined.

Figure 5:
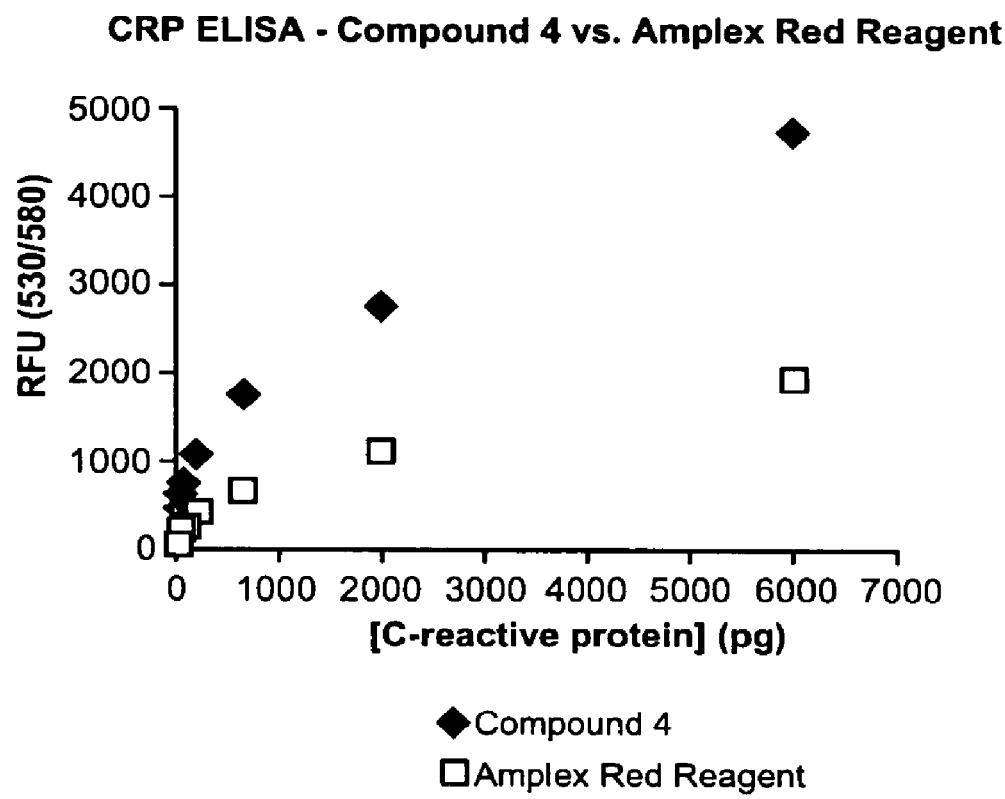
FIG. 5: is a plot comparing the relative fluorescent signal of Amplex Red reagent compared to Compound 4 in an ELISA for c-reactive protein using Goat anti-Rabbit IgG-HRP conjugate as a secondary antibody.

FIG. 5 demonstrates the ability of HRP conjugated to an anti-IgG to be used for the specific detection of c-reactive protein when a compound of the present invention in used as the fluorogenic compound. This figure also demonstrates the increased fluorescent signal using Compound 4 compared to non-fluorinated Amplex Red reagent. This methodology can be used to detect any specific analyte in an ELISA format with either the peroxidase conjugated to secondary antibody (or other antibody-binding protein) or primary antibody.

In other embodiments, the compounds according to Formula III (fluorescent dyes) are utilized for detection of an analyte in a sample or as a tracing or tracking reagent in a biological sample. In general, these compounds of the present invention are utilized to stain a sample to give a detectable optical response under desired conditions by first preparing a dye solution comprising a dye compound described above, at a concentration sufficient to yield a detectable optical response under the desired conditions. Specifically the methods for staining a sample comprises:
  a) contacting the sample with a fluorescent compound to prepare a labeled sample, wherein the fluorescent compound is according to formula III;
  b) incubating the labeled sample for a sufficient amount of time to prepare an incubated sample;
  c) illuminating the incubated sample with an appropriate wavelength to prepare an illuminated sample; and
  d) observing the illuminated sample whereby the sample is stained.

Optionally, the sample is washed to remove residual, excess or unbound dye. The dye compound typically forms a covalent or non-covalent association or complex with an element of the sample, or is simply present within the bounds of the sample or portion of the sample. In this instance the dye may be chemically reactive, conjugated to a carrier molecule, or conjugated to a solid support. Alternatively, the dye is not chemically reactive and is not conjugated to a carrier molecule or solid support. The dyes according to Formula III are intended to be used in any assay wherein a fluorescent compound finds use. Furthermore, the compounds according to Formula III can be used as spectrally matched controls for the compounds according to Formula II and IV. The following description of methods is meant to be illustrative but not as a limitation for the intended use.

In one embodiment, the staining is used to determine a specified characteristic of the sample by further comparing the optical response with a standard or expected response. For example, the dye solution is used to monitor specific components of the sample with respect to their spatial and temporal distribution in the sample. Alternatively, the dye preferentially binds to a specific analyte in a sample, enabling the researcher to determine the presence or quantity of that specific analyte. In another embodiment, the dye is used to analyze the sample for the presence of a mechanism that responds specifically to the dye compound, such as oxidation or reduction. The desired analysis to be performed determines the composition of the dye solution and chemical nature of the dye itself. In another example, the dye is bound by an antibody directed against the dye itself, typically resulting the fluorescence quenching of the dye.

For biological applications, the dye solution is typically an aqueous or mostly aqueous solution that comprises one or more of the described dye compounds. In one aspect of the invention, the dye solution comprises a fluorinated fluorophore or fluorogen as described above; alternatively, the dye solution comprises a dye compound that is a reactive dye analog, as previously described.

In yet another exemplary embodiment, the dye solution includes a dye conjugate as described above.

Solutions of the compounds of the invention are prepared according to methods generally known in the art. As with related known fluorophores and fluorogens, the dyes and dye-conjugates are generally soluble in water and aqueous solutions having a pH greater than or equal to about 6. Stock solutions of pure dyes, however, are typically dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. The labeling solution is prepared by diluting an aliquot of the stock solution into aqueous buffer to the desired labeling concentration. For those compounds that comprise amine- and/or thiol-reactive groups it is necessary to avoid buffers or mediums that contain amine- or thiol-containing molecules.

In general, the amount of dye or conjugate in the dye solution is the minimum amount required to yield detectable staining in the sample within a reasonable time, with minimal background fluorescence or undesirable staining. The exact concentration of dye or dye-conjugate to be used is dependent upon the experimental conditions and the desired results, and optimization of experimental conditions is typically required to determine the best concentration of stain to be used in a given application. The concentration of dye present in the dye solution typically ranges from nanomolar to micromolar. The required concentration for the dye solution is determined by systematic variation in dye or dye-conjugate concentration until satisfactory dye staining is accomplished. The starting ranges are readily determined from methods known in the art for use of similar compounds under comparable conditions for the desired optical response.

As stated above, the amount of dye added in the labeling solution is the minimum amount required to yield detectable cellular staining in the sample, without significant background fluorescence or staining of other nonselective structures such as organelles or cellular structures. The effects of overloading, or too much dye in a cell, may not be immediately apparent. For example, peripheral blood lymphocytes respond normally to concanavalin A when treated with up to 1 µM dye, but not more than with more than 5 µM dye. All cell types are different and the research will determine the concentration that is appropriate for each assay and cell type.

The amount of reagent required for staining eukaryotic cells depends on the number of cells present, the permeability of the cell membrane to the reagent and, in the case of the diaminodihydroxanthenes, the time required for intracellular metabolism to generate a fluorescent product. In the case of staining of tissues, the amount of reagent required may also vary with the accessibility of the reagent to the cells in the tissue. The required concentration for the labeling solution is determined by systematic variation in labeling concentration until a satisfactory fluorescent labeling is accomplished. Typically, the amount of fluorescent xanthylium reagent required is about 0.01 µM to about 50 µM, more typically about 0.5 µM to about 25 µM. Lower concentrations in the nanomolar range, such as from about 20 nM to about 500 nM, are typically employed when staining organelles such as mitochondria.

Low concentrations of dye will require longer incubation times for equivalent fluorescent brightness to be reached. For example, staining mitochondria incubated in 20 nM labeling solution will require about 1 to 2 hours to reach an arbitrary level of fluorescent staining that is reached in about 30 minutes using a 50 nM labeling solution. Similarly, the level of staining reached in 30 minutes using a 75 nM labeling solution of a diaminodihydroxanthene dye will require incubation for 90 minutes in a 50 nM labeling solution.

In another aspect, the thiol-chemically reactive compounds uniformly stain the cytoplasm of live cells, See for example Compound 30. In this application the compounds are well retained in living cells through several generations. They are inherited by daughter cells after cell fusion and are not transferred to adjacent cells in a population. In this instance, the cells are loaded with the present compounds by adding the labeling solution to the culture medium and then washing the cells briefly with fresh medium before analysis. The labeling solution is prepared by adding a stock solution to serum-free medium at a final contraction from about 0.1 µM to about 50 µM. For cells that are rapidly proliferating or dividing the assay will generally require a higher concentration of dye, typically from about 5 µM to about 50 µM, while a viability assay will typically require less dye, such as from about 0.1 µM to about 10 µM. Testing of at least a ten-fold range of concentration is recommended to determine the appropriate concentration for each particular assay.

Without wishing to be bound by a theory, it is likely that the thiol-reactive compounds are probably reacting with thiols in a glutathione S-transferase-mediated reaction. In many cells, glutathione levels are high and glutathione transferase is ubiquitous. The thiol-reactive compound is transformed into a cell-impermeant fluorescent dye-thioether adduct that can be fixed with aldehyde fixatives, permitting long-term storage.

Following preparation of the labeling solution, the solution is combined with the sample being analyzed. In one embodiment, the dyes of the present invention are cell permeant, and can be introduced into the sample cell or cells by incubation of the cell or cells in the labeling solution. Any other method of introducing the dye into the sample cell, such as microinjection of a labeling solution, scrape loading techniques (short mechanical disruption of the plasma membrane where the plasma membrane is peeled away from the cytoplasm, the dye is perfused through the sample and the plasma membrane reassembled), or patch clamp methods (where an opening is maintained in the plasma membrane for long periods) can be used. Any other treatment that will permeabilize the plasma membrane, such as electroporation, shock treatments or high extracellular ATP can be used to accelerate introduction of the dye into the cellular cytoplasm. Typically the dye will be introduced into the sample cell by incubation in the labeling solution, or by microinjection. Preferably the dye is introduced in to the cell or cells by incubation in the labeling solution. Microinjection of dye solution is used when analysis of a single cell is desired, within a colony of other sample cells.

The sample can be observed immediately after cellular or organelle staining is evident. After staining, the cells or isolated organelles in a sample can optionally be fixed. A number of fixatives and fixation conditions are suitable for practicing this invention. Useful fixatives include, but are not limited to, formaldehyde, paraformaldehyde, formalin, glutaraldehyde, cold methanol and 3:1 methanol:acetic acid. Typically, cell fixation is accomplished by incubating in a 3.7% solution of paraformaldehyde for about 15-30 minutes.

Fixation is optionally followed or accompanied by permeabilization, such as with acetone, ethanol, DMSO or various detergents. Permeabilization is utilized to allow bulky additional detection reagents to enter the cellular space (vida infra) that would ordinarily be impermeant with respect to the cellular membrane. A large variety of fixatives, fixation conditions, and permeabilization agents are known in the art, and other methods of fixing or permeabilizing sample cells in conjunction with the stains of the present invention will be obvious to one of ordinary skill. Cells and organelles stained by dyes of the present invention retain fluorescent staining even after fixation and extensive permeabilization.

Optionally, the cells or isolated organelles are washed to improve the results of the staining procedure. Washing the sample cell or cells after incubation in the labeling solution, or optionally after fixation or permeabilization, greatly improves the visualization of the cell and organelles. This is largely due to the decrease in non-specific background fluorescence after washing. Satisfactory organelle visualization is possible without washing at low labeling concentrations (for example <50 nM).

In one aspect of the invention, the dye solution comprises a fluorinated dye that non-covalently associates with organic or inorganic materials. Exemplary embodiments of the fluorinated dyes that possess a lipophilic substituent can be used to stain lipid assemblies such as biological membranes or liposomes by non-covalent incorporation of the dye compound within the membrane, e.g. for use as probes for membrane structure or for incorporation in liposomes, lipoproteins, films, plastics, lipophilic microspheres or similar materials.

The fluorinated compounds of the invention are useful as coloring agents, tracers for detecting the flow of fluids such as in angiography, and tracing of fluid flow through gap junctions of neurons according to procedures known in the art for other dyes. The fluorinated dyes of the invention are also useful in assays as haptens, according to known methods, because fluorination does not interfere with the recognition of the fluorophore by an anti-dye antibody.

The fluorinated reactive dye compounds of the invention can be used to cell surfaces, cell membranes or intracellular compartments such as organelles, or in the cell's cytoplasm, See for example Compound 28. Certain reactive groups allow the retention of the fluorophore in cells or organelles by reacting with cellular materials. In particular, haloalkyl- (Compound 30) or halomethylbenzamide-substituted fluorinated fluorophores are used to react selectively with intracellular components such as glutathione, or to retain the dye compounds within cells or within selected organelles where the dye compound is localized therein, according to methods previously described (U.S. Pat. No. 5,362,628 to Haugland et al, (1994); U.S. Pat. No. 5,576,424 to Mao et al. (1996) (in cells); and U.S. Pat. No. 5,459,268 to Haugland et al. (1995) and U.S. Pat. No. 5,686,261 to Zhang et al. (1997) (in mitochondria). Polyfluoroaryl-substituted dye compounds are similarly retained in cells, in part by covalent attachment. The reactive dyes are used to localize staining in a part of the sample, e.g., where the localization of the corresponding functional group is indicative of a characteristic of the sample; or to retain the dye in a specific portion of the sample for extended periods of time, e.g., to follow the stained portion of the sample through a period of time or sequence of events. Alternatively, the fluorinated reactive dyes are used according to this method to make dye-conjugates, as described above, that are separately useful for staining.

In an exemplary embodiment in which the dye solution comprises a dye-conjugate, the dye conjugate is a labeled member of a specific binding pair, and is used as a fluorescent probe for the complementary member of that specific binding pair, each specific binding pair member having an area on the surface or in a cavity which specifically binds to and is complementary with a particular spatial and polar organization of the other. For example, Compound 28 can be used to form a dye-conjugate ith an amine-containing molecule under conditions described above. The fluorescent conjugate of a specific binding pair member is useful for detecting and optionally quantifying the presence of the complementary specific binding pair member in a sample, by methods that are well known in the art. Optionally, the complementary binding pair member is present in an animal cell, plant cell, bacteria, yeast or virus. Alternatively, the complementary member is immobilized on a solid or semi-solid surface, such as a polymer, glass slide, hydrogel, polymeric membrane or polymeric particle (such as a polymeric bead). The dye-conjugate may also comprise a fluorinated dye in a blocked form wherein the block is later removed by the action of an enzyme or light, or the conjugate may be one in which $OR^8$ is OH, in which case detection is made following oxidation of the probe to a fluorescent dye.

Representative specific binding pairs are shown in Table 2. Typically a specific binding pair member conjugated to the dye is a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. The reactive dyes are used according to methods extensively known in the art, to prepare antibody conjugates for use in microscopy and immunofluorescent assays and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and WO Appl. 94/05688 to Menchen, et al., and a wide variety of other applications). Nucleotide conjugates are readily incorporated by DNA polymerase and can be used for in situ hybridization or other techniques.

The compounds of the invention are also of use in the numerous fluorescence polarization assays that use conjugates of fluorescent dyes to low molecular weight drugs and ligands, which will be improved by the use of the fluorinated dye compounds of the invention, e.g., U.S. Pat. No. 4,420,568 to Wang (1983) and U.S. Pat. No. 4,510,251 to Kirkemo et al. (1985).

In those embodiments in which a fluorinated dye is conjugated to a specific binding pair member that is a chelator of calcium, sodium, magnesium, potassium, or other biologically important metal ion, the dye-conjugate functions as an indicator of the ion, which indicators are optionally further conjugated to a biological or plastic polymer according to methods known in the art; e.g., using fluorinated analogs of the compounds described in U.S. Pat. No. 5,453,517 to Kuhn, et al. (1995); U.S. Pat. No. 5,405,975 to Kuhn, et al. (1995). Alternatively, the dye itself acts as a pH indicator at pH values within about 1.5 pH units of the individual dye's pKa. Typically the detectable optical response of the ion indicators is a change in fluorescence.

In another exemplary embodiment, the dye compounds are fluorinated dyes that are substrates for oxidative enzymes and other reactive oxidizing agents, particularly for peroxidase enzymes.

The fluorinated enzyme substrates optionally contain additional substituents that provide additional advantages. Fluorinated fluorophores modified to contain a lipophilic tail according to the synthesis described in U.S. Pat. No. 5,208, 148 to Haugland et al. (1993) (incorporated by reference), are useful for permeabilizing substrates for intracellular enzymes.

In another exemplary embodiment of the invention, the compounds are used to determine the efficiency of a cellular efflux pump of cells in a sample. Preferably the dye compounds are diacetates or diphosphates. The dye compound is used in the minimum concentration that gives a detectable fluorescence emission. Once the diacetate compounds are inside the cell, the blocking acetates are cleaved and the compound becomes highly fluorescent.

The efficiency of the cellular efflux pump of cells in the sample is determined by comparing the fluorescence emission of cells in the sample with the fluorescence of cells having a known efflux efficiency. Where the efflux pump is impaired, inhibited, or absent, the fluorescent compound is well retained in the cell; where the efflux pump is present and functioning, the fluorescence of the cells decreases markedly. The photostability of the present fluorinated compounds is advantageous for monitoring the time course of fluorescence.

Another application where the enhanced photostability of the present fluorinated dye compounds is particularly advantageous is use of the dye compounds for tracing. One or more fluorinated dyes conjugated to a biologically compatible polymer, including amino acid polymers (typically proteins, including fluorescent proteins), carbohydrate polymers (typically dextrans), and polymeric microspheres (typically polystyrene) are readily prepared for use as tracers according to methods known in the art.

The dye compounds are advantageously used to stain biological samples, i.e. samples that comprise biological components. In one embodiment of the invention, the sample comprises heterogeneous mixtures of components, including intact cells, cell extracts, bacteria, viruses, organelles, and mixtures thereof. In another aspect of the invention, the sample comprises a single component or homogeneous group of components, e.g. biological polymers such as amino acid polymers, nucleic acid polymers or carbohydrate polymers, or lipid membrane complexes, whether the polymers are synthetic or natural.

The sample is typically stained by passive means, i.e., by incubation with the dye solution. Any other method of introducing the dye into the sample, such as microinjection of a dye solution into a cell or organelle, can be used to accelerate introduction of the dye into the sample. The dyes of the present invention are generally non-toxic to living cells and other biological components, within the concentrations of use.

The sample can be observed immediately after staining. The sample is optionally combined with other solutions in the course of staining, including wash solutions, permeabilization and/or fixation solutions, and other solutions containing additional detection reagents. Washing following staining generally improves the detection of the optical response due to the decrease in non-specific background fluorescence after washing. Satisfactory visualization is possible without washing by using lower labeling concentrations. A number of fixatives and fixation conditions suitable for practicing this invention are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the dyes described above are well retained in cells, and sample cells stained with these dyes retain considerable fluorescent staining after fixation. Fixation is optionally followed or accompanied by permeabilization, such as with acetone, ethanol, DMSO or various detergents, to allow bulky dye compounds, including dye-conjugates described above, to cross cell membranes, according to methods generally known in the art. The staining of the present invention is optionally combined with the use of an additional detection reagent that produces a detectable response due to the presence of a specific cell component, intracellular substance, or cellular condition, according to methods generally known in the art. Where the additional detection reagent has spectral properties that differ from those of the subject dye compounds, multicolor applications are possible.

The compounds of the invention are also of use to derivative low molecular weight compounds for their analysis by capillary zone electrophoresis (CZE), HPLC or other separation techniques.

In another embodiment, the compounds according to Formula IV are used to measure the viability of a cell culture. In this instance, the fluorogenic compounds are taken up by live cells and oxidized by the metabolic activity of the cells wherein fluorogenic compounds are converted to fluorescent product.

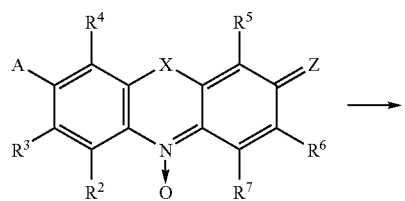

-continued

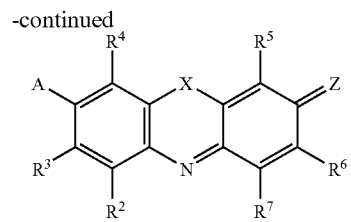

Therefore, a method of the present invention comprises a) contacting the sample with a compound according to Formula IV to prepare a labeled sample; b) incubating the labeled sample for a sufficient amount of time to prepare an incubated sample, wherein the compound is capable of entering cells and being reduced to produce a fluorescent product; c) illuminating the incubated sample with an appropriate wavelength; and d) observing the illuminated sample whereby the metabolic activity is detected and the resulting signal is proportional to the number of viable cells present in the sample.

These compounds represent by Formula IV can be used in any method for measuring metabolic activity of a cell including, but not limited to cell proliferation assays and cell viability assays. In the case of cell proliferation, the internal environment of proliferating cells is more reduced than that of non-proliferating cells. Specifically, the ratios of NADPH/NADP, FADH/FAD, FMNH/FMN and NADH/NAD, increase during proliferation. Compounds according to Formula IV, which can be reduced by these metabolic intermediates, are useful for monitoring cell proliferation because their reduction is accompanied by a measurable shift in color, See Example 46.

Illumination

At any time after or during an assay or staining procedure, the sample is illuminated with a wavelength of light that results in a detectable optical response, and observed with a means for detecting the optical response. While the dye compounds are detectable calorimetrically, using ambient light, typically the dye compounds are detected by the fluorescence properties of the parent fluorophore. Upon illumination, such as by an ultraviolet or visible wavelength emission lamp, an arc lamp, a laser, or even sunlight or ordinary room light, the dye compounds, including dye compounds bound to the complementary specific binding pair member, display intense visible absorption as well as fluorescence emission. Selected equipment that is useful for illuminating the dye-conjugates of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This calorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorinated dye compound and a second fluorophore with detectably different optical properties, typically by distinguishing the fluorescence response of the fluorinated dye-conjugate from that of the second fluorophore. Where the sample is examined using a flow cytometer, examination of the sample optionally includes isolation of particles within the sample based on the fluorescence response of the dye compound by using a sorting device.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or x-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample or in a localized portion of the sample. The presence or absence of the optical response after the elapsed time is indicative of one or more characteristic of the sample. Comparison of the degree of staining with a standard or expected response can be used to determine whether and to what degree the sample possesses a given characteristic.

Sample Preparation

The end user will determine the choice of the sample and the way in which the sample is prepared. The sample includes, without limitation, any biological derived material or aqueous solution that is thought to contain a target analyte, peroxide or an enzymatic system that produces peroxide. The samples may also include a reactive oxygen species, e.g., peroxide, or a molecule or system, e.g., an enzymatic system that produces peroxide. Furthermore, the sample can include a buffer solution that contains a peroxidase, peroxide and fluorogenic compounds of the present invention to determine the ability of the sample to oxidize the compound of the invention.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons.

In an exemplary embodiment, for carrying out the assay, the enzyme concentration is conveniently in the range of about 1 nM to 500 nM, more usually in the range of about 25 to 250 nM. One may use an individual fluorogenic substrate or a mixture of substrates in order to determine the substrate profile of the enzyme. The concentration range of each substrate will be about 10 to 5000 µM, more usually 50 to 2000 µM.

Coenzyme, if any, is preferably present in excess, so as not be rate limiting. Generally, with the concentrations of enzyme indicated above, the concentration of coenzyme will be at least about 0.1 mM, usually at least about 1 mM and not more than about 25 mM. The coenzyme solution should be prepared freshly for each series of determinations.

Various buffers may be used that do not interfere with the enzyme activity. These buffers include PBS, Tris, MOPS, HEPES, phosphate, etc. The pH will vary depending upon the particular monooxygenase being assayed, generally being in the range of about 7.0-7.5, where the pH is selected to provide for at least about maximum enzyme activity. The concentration of buffer will be sufficient to prevent a significant change in pH during the course of the reaction, generally being in the range of about 0.1 to 100 mM, more usually 0.5 to 50 mM.

The reaction time will usually be at least about 5 min, more usually at least about 30 min and preferably not more than about 120 min, depending upon the temperature, concentrations of enzyme and substrate, etc. By using a specific time period for the reaction or measuring the fluorescence at 2 different times, the rate of reaction can be determined for comparison with other determinations. The temperature will generally be in the range of about 20 to 50° C., more usually in the range of about 25 to 40° C.

In certain instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

After sufficient time for a detectable amount of product to form, the reaction is optionally quenched. Various quenching agents may be used, both physical and chemical. Conveniently, a small amount of a water-soluble inhibitor may be added, such as acetonitrile, DMSO, SDS, methanol, DMF, etc. The amount of inhibitor will vary with the nature of the inhibitor and may be determined empirically.

Kits

In another aspect, the present invention provides kits that include a fluorogenic or fluorescent compound of the invention. The kit will generally also include instructions for using the compound of the invention in one or more methods.

In an exemplary embodiment, the kit includes a reactive compound of the invention and instructions for conjugating the dye to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g. proteins, oligonucleotides or carbohydrates), polymeric resins and plastics (e.g. polystyrene), metals, glasses, and other organic or inorganic substances. The dyes of the present invention are well-suited for the preparation of such a kit.

In another exemplary kit of the invention, the instructions provided are for performing an assay that detects oxidative or reductive agents or conditions in a sample. For example, in one embodiment, directions are provided for detecting a reactive oxygen species, or an enzyme, organism, or other agent that generates a reactive oxygen species in a sample. In one aspect the kit further comprises an enzyme, a catalyst, a reaction buffer, an enzyme substrate, a peroxide, a stop solution, or a positive control. In one aspect the enzyme has oxidase or peroxidase activity and the positive control is a compound according to formula III.

In another exemplary kit of the invention, the instructions provided are for performing an ELISA wherein a peroxidase is conjugated to a carrier molecule and a compound according to formula II is provided as the fluorogenic substrate. In an exemplary embodiment the peroxidase is HRP. In one aspect the carrier molecule is an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus. In a further aspect, the carrier molecule is an antibody or fragment thereof, an avidin or streptavidin, a biotin, a blood component protein, a dextran, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide. In another aspect the carrier molecule specifically associates with the analyte, such as a primary antibody the binds the target analyte. Alternatively, the carrier molecule binds to the primary antibody, such as anti-IgG, anti-IgE or anti-IgA.

A detailed description of the invention having been provided above, the following examples are given for the purpose of illustrating the invention and shall not be construed as being a limitation on the scope of the invention or claims.

EXAMPLES

Example 1

Preparation of Compound 1

To a solution of 4-fluororesorcinol (W.-C. Sun, et al., *J. Org. Chem.*, 62 (1997) 6469) in ethanol (100 mL) at 0° C. was added a solution of KOH (3.0 g, 53.3 mmol) in $H_2O$. Isoamyl nitrite (5.5 mL, 40.9 mmol) was then added dropwise and the combined solution was allowed to warm to room temperature and stirred for an additional 1 hr.

The solution was concentrated in vacuo to a thick oil. The oil was dissolved in 1 M HCl (200 mL), stirred for 1 hr and filtered to remove undissolved impurities. The filtrate was extracted with ethyl acetate (200 mL). The organic layer was washed with saturated NaCl (200 mL) and dried over anhydrous sodium sulfate. The filtrate was evaporated to a yellow-brown powder. The solid was stirred in dichloromethane for 48 hrs, filtered and dried to a constant weight to give 6-nitroso-4-fluororesorcinol (3.11 g, 84% yield), Compound 1. $^1$H NMR (DMSO-$d_6$): 13.78 (1H, s, OH); 11.46 (1H, s, OH); 7.19 (1H, d, J=3 Hz); 5.76 (1H, d, J=2 Hz).

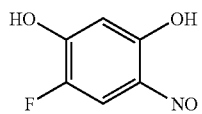

Compound 1

Example 2

Preparation of Compound 2
(2,8-Difluoro-3,7-dihydroxyphenoxazine Triethylammonium salt)

A mixture of 1 (2.56 g, 16.3 mmol) and 4-fluororesorcinol (2.07 g, 16.3 mmol) in concentrated sulfuric acid (12 mL) was heated at 80° C. for 1 hr. The reaction was cooled to room temperature and added to saturated NaCl (150 mL) at 0° C. The mixture was stirred for 40 min and then filtered. The residual solids were dissolved in methanol (200 mL) and the solution was adjusted to pH 9 with triethylamine. The resultant solution was adsorbed on silica gel and concentrated to dryness in vacuo. The material was purified on a silica gel column using 80% chloroform/19% methanol/1% triethylamine as the eluent. Purified material was dried to a constant weight to give phenoxazine 2 (3.1 g, 70% yield). $^1$H NMR (DMSO-$d_6$) 9.21 (1H, broad s); 7.40 (2H, d, J=3 Hz); 6.47 (2H, d, J=2); 3.10 (6H, q); 1.20 (9H, t).

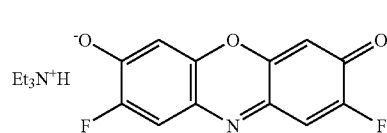

Compound 2

Example 3

Preparation of Compound 3
(2,8-Difluoro-3,7,10-triacetylphenoxazine)

To a mixture of tin (II) chloride (1.45 g, 7.6 mmol) and 2 (505 mg, 1.4 mmol) in triethylamine (1.6 mL) was added acetic anhydride (10 mL, 105 mmol). The mixture was heated to reflux for 20 min, cooled to room temperature and filtered. The filtrate was diluted with ethyl acetate (20 mL) and saturated bicarbonate solution (20 mL) and stirred at room temperature overnight. The organic layer was washed with 1 M HCl (2×100 mL) and then saturated NaCl (2×100 mL). The organic layer was dried over anhydrous sodium sulfate and evaporated to a brown oily semi-solid. Purification by silica gel chromatography with methylene chloride as eluent afforded 72 mg (14% yield) of pure material (3) after drying. $^1$H NMR (CDCl$_3$): 7.34 (2H, d, J=3 Hz); 6.95 (2H, d, J=2 Hz,); 2.39 (3H, s); 2.37 (6H, s)

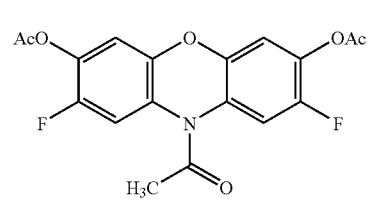

Compound 3

Example 4

Preparation of compound 4
(2,8-Difluoro-10-acetyl-3,7-dihydroxyphenoxazine)

To a solution of 3 (70 mg, 195 mmol) in $CH_2Cl_2$ and $CH_3OH$ (10 mL, 1:1) was added sodium methoxide (1.1 eq) in methanol. The solution was stirred at room temperature for 10 minutes. The solution was then adsorbed onto silica gel and purified by silica gel chromatography using 5% methanol in methylene chloride as the eluent to give 14 mg of Compound 4. $^1$H NMR (DMSO-$d_6$) 10.27 (2H, broad s, OH); 7.43 (2H, d, J=3 Hz), 6.74 (2H, d, J=2 Hz); 2.25 (3H, s); $^{19}$F NMR (DMSO-$d_6$)-141.5 (2F, s).

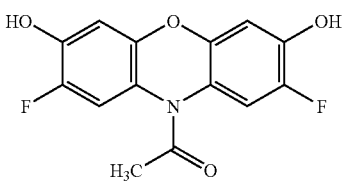

Compound 4

Example 5

Preparation of Compound 5

A mixture of 2,4-difluororesorcinol (0.10 g, 0.68 mmol) and 4-nitrosoresorcinol (95 mg, 0.68 mmol) was prepared in concentrated sulfuric acid (2 mL) on ice. The resulting mixture was heated to 80° C. with magnetic stirring for 36 hours, then cooled and diluted with water (40 mL). The resulting mixture was extracted with 3% methanol/ethyl acetate (3×10 mL). The extract was dried over sodium sulfate, filtered through Celite and concentrated to give 5 as 70 mg of a red powder: fluorescence emission max 593 nm (excited at 560 nm, pH 9).

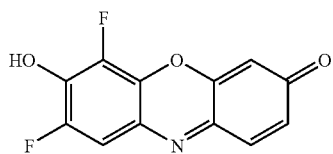

Compound 5

Example 6

Preparation of Compound 6

A mixture of 2-fluororesorcinol (0.10 g, 0.78 mmol) and 4-nitrosoresorcinol (109 mg, 0.78 mmol) was prepared in concentrated sulfuric acid (2 mL). The resulting mixture was heated to 80° C. with magnetic stirring for 36 hours, then cooled and diluted with water (50 mL). The resulting mixture was extracted with ethyl acetate (3×30 mL). The extract was washed with water (1×20 mL) and brine (1×20 mL), dried over sodium sulfate, and concentrated to give 6 as 40 mg of a red powder: fluorescence emission max 597 nm (excited at 560 nm, pH 9).

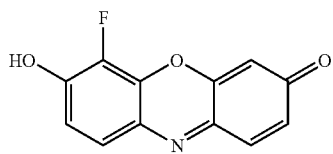

Compound 6

Example 7

Preparation of Compound 7

A mixture of 4-fluororesorcinol (0.10 g, 0.78 mmol) and 4-nitrosoresorcinol (0.11 g, 0.78 mmol) was prepared in concentrated sulfuric acid (3 mL). The resulting mixture was heated to 70° C. with magnetic stirring for 24 hours, then cooled and diluted with water (60 mL). The resulting mixture was extracted with ethyl acetate (2×40 mL) and ether (2×40 mL). The combined extracts were washed wither water (1×20 mL) and brine (1×20 mL), dried over sodium sulfate, and concentrated to give 7 as 30 mg of a red solid: fluorescence emission max 586 nm (excited at 560 nm, pH 9).

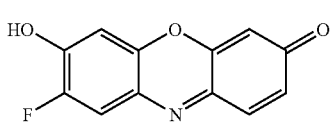

Compound 7

Example 8

Preparation of Compound 8

A mixture of 5-fluororesorcinol (0.10 g, 0.78 mmol) and 4-nitrosoresorcinol (0.11 g, 0.78 mmol) was prepared in concentrated sulfuric acid (3 mL). The resulting mixture was heated to 110° C. with magnetic stirring for 24 hours, then cooled and diluted with water (50 mL). The resulting mixture was extracted with ethyl acetate (2×20 mL). The extract was washed wither water (1×10 mL) and brine (1×10 mL), dried over sodium sulfate, and concentrated to give 8 as 5 mg of a red residue: fluorescence emission max 585 nm (excited at 560 nm, pH 9).

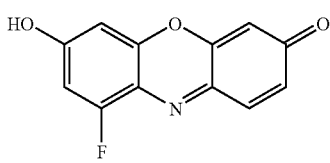

Compound 8

Example 9

Preparation of Compound 9

A mixture of 2,4,5-trifluororesorcinol (0.10 g, 0.61 mmol) and 4-nitrosoresorcinol (85 mg, 0.61 mmol) was prepared in concentrated sulfuric acid (2 mL). The resulting mixture was heated to 150° C. with magnetic stirring for 4.5 hours, then cooled and diluted with 1:1 brine/water (100 mL). The resulting mixture was extracted with ethyl acetate (2×20 mL) and ether (1×20 mL). The combined extracts were washed wither water (1×10 mL) and brine (1×10 mL), filtered through Celite, dried over sodium sulfate, and concentrated to give Compound 9 as 79 mg of a red solid: emission max 589 nm (excited at 560 nm, pH 9).

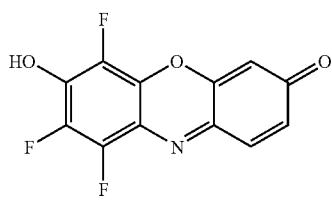

Compound 9

Example 10

Photostability Study of Compounds 5-9

Compounds 5-9, fluorinated resorufin compounds, exhibited unexpectedly improved photostability over unsubstituted resorufin. For example, solutions of each were matched by optical density (0.03 at 560 nm in aqueous buffer at pH 9), then continuously irradiated in a spectrofluorimeter at 560 nm for 30 minutes. Over the duration of the experiment, resorufin photobleached to a greater extent than any of the fluorinated analogs. The rank order of photostability of fluourinated analogs is indicated in Table 3.

TABLE 3

| | Relative Photostability |
|---|---|
| Compound | Fluorescence remaining after irradiation for 30 minutes at 560 nm |
| Compound 9 | 98% |
| Compound 6 | 97% |
| Compound 5 | 96% |
| Compound 8 | 95% |
| Compound 7 | 94% |
| resorufin | 91% |

Example 11

Preparation of Compound 10

To a solution of 2-fluororesorinol (1.5 g, 11.7 mmol) in ethanol (50 mL) at 0° C. was added a solution of KOH (1.5 g, 26.6 mmol) in H$_2$O (5 mL). Isoamyl nitrite (2.8 mL, 20.5 mmol) was then added dropwise and the combined solution was allowed to warm to room temperature and stirred for an additional 1 hr. The solution was concentrated in vacuo to a thick oil. The oil was dissolved in 1 M HCl (100 mL), stirred for 1 hr and filtered to remove un-dissolved impurities. The filtrate was extracted with ethyl acetate (200 mL). The organic layer was washed with saturated NaCl (200 mL) and dried over anhydrous sodium sulfate. The filtrate was evaporated to a yellow-brown powder. The solid was stirred in dichloromethane for 24 hrs, filtered and dried to a constant weight to give 10 (1.3 g).

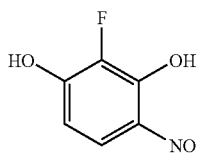

Compound 10

Example 12

Preparation of Compound 11

A mixture of 6-nitroso-2-fluororesorcinol 10 (1.25 g, 8.1 mmol) and 2-fluororesorcinol (1 g, 8.1 mmol) in concentrated sulfuric acid (6 mL) was heated at 80° C. for 1 hr. The reaction was cooled to room temperature and added to saturated NaCl (150 mL) at 0° C. The mixture was stirred for 40 min and then filtered. The residual solids were dissolved in methanol (100 mL) and the solution was adjusted to pH 9 with triethylamine. The resultant solution was adsorbed on silica gel and concentrated to dryness in vacuo. The material was purified on a silica gel column using 80% chloroform/19% methanol/1% triethylamine as the eluent. Purified material was dried to a constant weight to give the phenoxazine 11 (1.1 g).

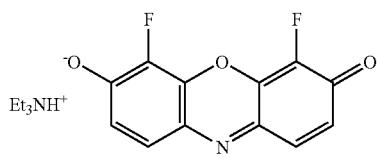

Compound 11

Example 13

Preparation of Compound 12

2,4-Difluororesorcinol (2 g, 13.7 mmol) was converted to 6-nitroso-2,4-difluororesorcinol 12 (1 g) using the procedure for preparing 10.

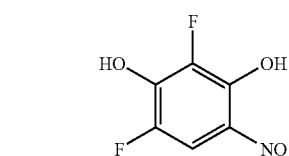

Compound 12

Example 14

Preparation of Compound 13

A mixture of 6-nitroso-2,4-difluororesorcinol 12 (1 g, 5.34 mmol) and 2,4-difluororesorcinol (0.78 g, 5.34 mmol) in concentrated sulfuric acid (6 mL) was heated at 80° C. for 1 hr. The reaction was cooled to room temperature and added to saturated NaCl (150 mL) at 0° C.

The mixture was stirred for 40 min and then filtered. The residual solids were dissolved in methanol (100 mL) and the solution was adjusted to pH 9 with triethylamine. The resultant solution was adsorbed on silica gel and concentrated to dryness in vacuo. The material was purified on a silica gel column using 80% chloroform/19% methanol/1% triethylamine as the eluent. Purified material was dried to a constant weight to give the phenoxazine 13 (0.8 g).

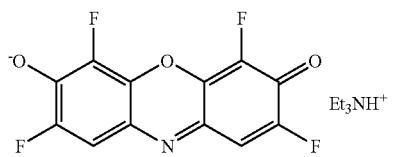

Compound 13

Example 15

Preparation of Compound 14

**To a solution of 5-fluororesorinol (1.5 g, 11.7 mmol) in ethanol (50 mL) at 0° C. was added a solution of KOH (1.5 g, 26.6 mmol) in $H_2O$ (5 mL). Isoamyl nitrite (2.8 mL, 20.5 mmol) was then added dropwise and the combined solution was allowed to warm to room temperature and stirred for an additional 1 hr. The solution was concentrated in vacuo to a thick oil. The oil was dissolved in 1 M HCl (100 mL), stirred for 1 hr and filtered to remove insoluble impurities. The filtrate was extracted with ethyl acetate (200 mL). The organic layer was washed with saturated NaCl (200 mL) and dried over anhydrous sodium sulfate. The filtrate was evaporated to a yellow-brown powder. The solid was stirred in dichloromethane for 24 hrs, filtered and dried to a constant weight to give 14 (1.6 g).

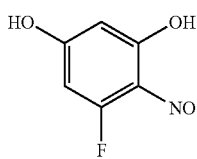

Compound 14

Example 16

Preparation of Compound 15

A mixture of 6-nitroso-5-fluororesorcinol 14 (1.25 g, 8.1 mmol) and 5-fluororesorcinol (1 g, 8.1 mmol) in concentrated sulfuric acid (6 mL) was heated at 80° C. for 1 hr. The reaction was cooled to room temperature and added to saturated NaCl (150 mL) at 0° C. The mixture was stirred for 40 min and then filtered. The residual solids were dissolved in methanol (100 mL) and the solution was adjusted to pH 9 with triethylamine. The resultant solution was adsorbed on silica gel and concentrated to dryness in vacuo. The material was purified on a silica gel column using 80% chloroform/19% methanol/1% triethylamine as the eluent. Purified material was dried to a constant weight to give the phenoxazine 15 (0.8 g).

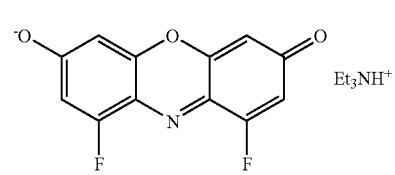

Compound 15

Example 17

Preparation of Compound 16

To a solution of 4-chlororesorcinol (10 g, 69.4 mmol) in ethanol (50 mL) at 0° C. was added a solution of KOH (5.1 g, 76.3 mmol) in $H_2O$ (10 mL). Isoamyl nitrite (10.3 mL, 90.2 mmol) was then added dropwise and the combined solution was allowed to warm to room temperature and stirred for an additional 1 hr. The solution was acidified to pH 2 with 10% HCl. The solid precipitate was collected by suction filtration and dried to a constant weight to give 16 (5.5 g).

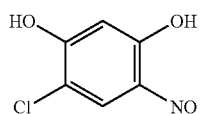

Compound 16

Example 18

Preparation of Compound 17

A mixture of 6-nitroso-4-chlororesorcinol 16 (0.5 g, 2.9 mmol) and 4-chlororesorcinol (0.46 g, 3.19 mmol) in concentrated $H_2SO_4$ (3 mL) was stirred at room temperature for 1 hr and then heated at 110° C. for 30 minutes. After cooling to room temperature, the reaction mixture was poured into ice-water. The precipitate was collected by suction filtration and dried to a constant weight to give 17 (0.6 g).

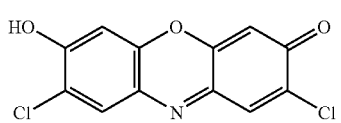

Compound 17

Example 19

Preparation of Compound 18

A suspension of 2,8-dichloro-3,7-dihydroxyphenoxazine 17 (0.2 g, 0.7 mmol) and tin (II) chloride (0.269 g, 1.4 mmol) in acetic anhydride (10 mL) was heated at 130° C. for 2 hrs and then cooled down to room temperature. The mixture was diluted with water and extracted with ethyl acetate (2×50 mL). The combined organic layers were washed with 1 M HCl (50 mL), saturated NaCl (50 mL) and dried with anhydrous sodium sulfate. The crude product was purified by silica gel column using chloroform as eluent to give 18 (80 mg).

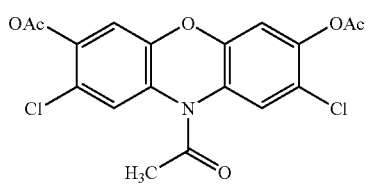

Compound 18

Example 20

Preparation of Compound 19

To a solution of 2,8-chloro-3,7,10-triacetylphenoxazine 18 (80 mg, 0.2 mmol) in $CH_2Cl_2$ and $CH_3OH$ (4 mL, 1:1) was added sodium methoxide (1.1 eq) in methanol. The solution was stirred at room temperature for 10 minutes. The solution was then adsorbed on silica gel and purified by silica gel chromatography using 5% methanol in methylene chloride as the eluent to give 19 (14 mg).

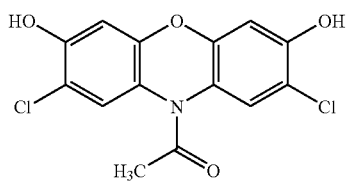

Compound 19

Example 21

Preparation of Compound 20

A suspension of 6-nitroso-4-chlororesorcinol 16 (0.5 g, 2.9 mmol) and 2-carboxyresorcinol (0.445 g, 2.9 mmol) in concentrated sulfuric acid (3 mL) was heated at 110° C. for 30 minutes. After cooling down to room temperature, the mixture was poured into ice water and the product was collected by suction filtration and dried to constant weight to give 20 (0.25 g).

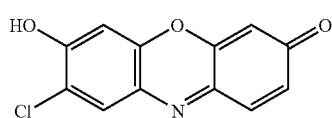

Compound 20

Example 22

Preparation of Compound 21

To a suspension of 2-chloro-6-carboxy-3,7-dihydroxyphenoxazine 20 (0.5 g, 1.95 mmol) and succinimidyl trifluoroacetate (0.49 g, 2.34 mmol) in dry THF (10 mL) was added pyridine (0.32 mL, 2.34 mmol). The mixture was stirred at room temperature overnight and concentrated to dryness. The residue was suspended in ethyl acetate and stirred at room temperature for 1 h. The precipitate was collected by suction filtration and dried to a constant weight to give 21 (0.35 g), used for the next step without further purification.

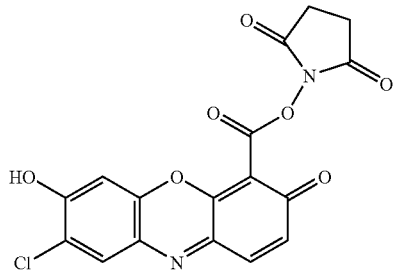

Compound 21

Example 23

Preparation of Compound 22

To a solution of 2-fluoro-8-dodecylresorufin (0.4 g, 1 mmol) in TFA (10 mL) was added hydrogen peroxide-urea (1.5 g, 15 mmol). The mixture was stirred at room temperature for 5 h and then was poured into water. The aqueous layer was extracted with ethyl acetate (2×50 mL). The combined organic layers were washed with water (30 mL), saturated NaCl (30 mL) and dried with anhydrous $Na_2SO_4$. The crude product was purified by column chromatography on silica gel using $CHCl_3$ and 2% MeOH in $CHCl_3$ as eluents to give compound 22 (30 mg).

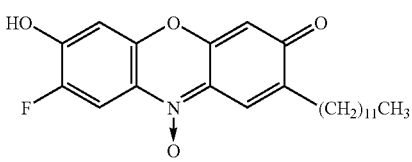

Compound 22

Example 24

Preparation of Compound 23

To a 100 mL flask, methyl 4-bromobenzoate (1.42 g), 2,4-dimethoxybenzeneboronic acid (1.3 g), Pd $(OAc)_2$ (100 mg), $K_2CO_3$ (1.9 g) and tetrabutylammonium bromide (3.54 g) were added. The flask was flushed with $N_2$ and sealed with a rubber septum. Water (50 mL) was added with a syringe, and the resulting suspension was stirred and deoxygenated with $N_2$ at room temperature. The mixture was stirred and heated for 40 min. at 80° C. under $N_2$, cooled to room temperature, and acidified to pH 1 with concentrated HCl. The precipitate (Pd) was filtered off and washed with EtOAc. The filtrate was extracted with EtOAc, washed with saturated brine, dried over anhydrous $Na_2SO_4$ and concentrated to give crude product 23.

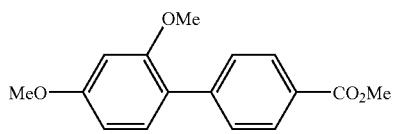

Compound 23

Example 25

Preparation of Compound 24

To the crude 23 in a flask, 48% HBr in water (20 mL) and AcOH (20 mL) were added and the mixture was refluxed for 3 h under $N_2$. The resulting mixture was cooled to room temperature and poured into water (200 mL). The solution was extracted with EtOAc. The EtOAC layer was washed with brine and dried over anhydrous $Na_2SO_4$. The EtOAc extract was concentrated in vacuo and purified on a silica gel column using 10:1 $CHCl_3$/MeOH and 5:1 $CHCl_3$/MeOH as eluents to give compound 24 (0.97 g).

Compound 24

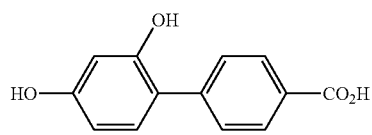

Example 26

Preparation of Compound 25

To compound 24 (0.97 g) in concentrated $H_2SO_4$ (20 mL) under $N_2$ was added 4-fluoro-6-nitrosoresorcinol (0.59 g). The mixture was heated for 2 h at 80° C. under $N_2$ and then poured into crushed ice/water. The suspension was extracted with EtOAc. The EtOAc layer was washed with brine and dried over anhydrous $Na_2SO_4$. The EtOAc extract was concentrated in vacuo and purified on a silica gel column using $CHCl_3$, 10:1 $CHCl_3$/MeOH and 500:100:1 $CHCl_3$/MeOH/AcOH as eluents to give compound 25 (0.83 g).

Compound 25

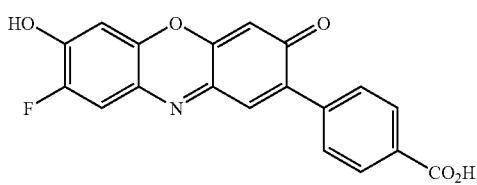

Example 27

Preparation of Compound 26

To compound 25 (1.0 g) in AcOH (30 mL) and triethylamine (5 mL), tin (II) chloride dihydrate (5.0 g) was added and refluxed for 1 h. The resulting reaction mixture was cooled to 70° C. and then diluted with EtOAc (200 mL). The mixture was cooled to room temperature and poured into crushed ice/water. The precipitate was filtered off and washed with EtOAc. The filtrate was extracted with EtOAc. The EtOAc layer was washed with saturated brine, dried over anhydrous $Na_2SO_4$ and concentrated to dryness. The crude product was purified on a silica gel column using $CHCl_3$, 100:1 $CHCl_3$/MeOH and 50:1 $CHCl_3$/MeOH as eluents to give compound 26 (214 mg).

Compound 26

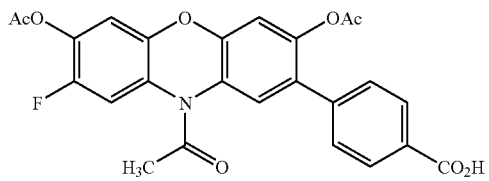

Example 28

Preparation of Compound 27

To compound 26 (55 mg) in MeCN (10 mL)/MeOH (3 mL), $K_2CO_3$ (140 mg) was added and stirred for 2 h at room temperature under $N_2$ in the dark. The resulting mixture was diluted with water (100 mL) and acidified with AcOH to pH 2. The solution was extracted with EtOAc. The EtOAc layer was washed with brine and dried over anhydrous $Na_2SO_4$. The EtOAc extract was concentrated in vacuo and purified on a silica gel column using 10:1 $CHCl_3$/MeOH and 5:1 $CHCl_3$/MeOH as eluents to give compound 27 (16 mg).

Compound 27

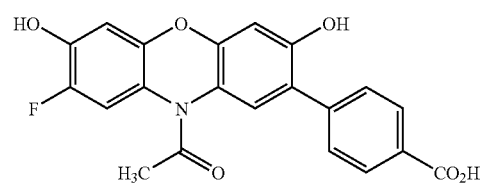

Example 29

Preparation of Compound 28

To compound 27 (50 mg) in dry DMF (5 mL) under $N_2$ in the dark, EDC (30 mg) and N-hydroxysuccinimide (18 mg) were added and the mixture was stirred for 5 h. The solvent was removed in vacuo and the residue was purified on a short silica gel column under $N_2$ in the dark using 10:1 $CHCl_3$/MeOH and 5:1 $CHCl_3$/MeOH as eluents to give compound 28 (32 mg).

Compound 28

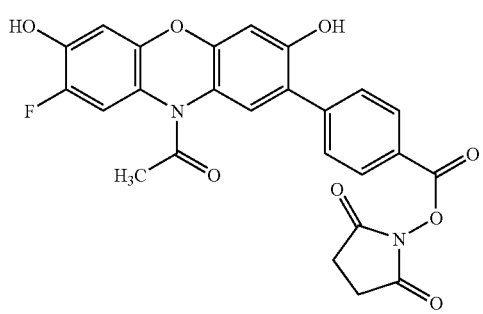

Example 30

Preparation of Compound 29

To compound 26 (20 mg) in dry THF (6 mL) at 0° C., ethyl chloroformate (0.05 mL) and triethylamine (0.05 mL) were added. The mixture was stirred for 1 h at RT. The white precipitate was filtered off, and washed with dry THF. The filtrate was concentrated to dryness. The residue was re-dissolved in dry THF (6.0 mL), and then $NaBH_4$ (100 mg) in EtOH (1.0 mL) was added at 0° C. The mixture was stirred for 3 h at room temperature and then NaOH (1.0 N, 5.0 mL) was added. The solution was heated for 4 h at 60° C., and acidified to pH=3 with 10% HCl. The solution was diluted with water (100 mL) and extracted with EtOAc. The EtOAc extract was washed with brine, dried over anhydrous $Na_2SO_4$ and concentrated in vacuo. The residue was purified on a silica gel column using 20:1 $CHCl_3$/MeOH and 10:1 $CHCl_3$/MeOH as eluents to give compound 29 (10 mg).

Compound 29

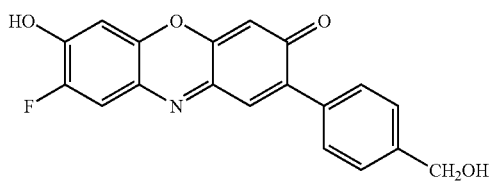

Example 31

Preparation of Compound 30

To compound 29 (10 mg) in THF (3 mL), con. HCl (10 mL) was added. The mixture was stirred for 2 days at room temperature. The solution was concentrated to dryness in vacuo. The residue was purified by a preparative silica gel TLC using 30:1 $CHCl_3$/MeOH as developing solvents to give compound 30 (6 mg).

Compound 30

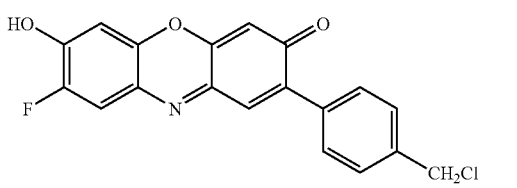

Example 32

Preparation of Compound 31

To compound 27 (60 mg) in dry DMF (10 mL) under $N_2$ in the dark, EDC (30 mg) and N-hydroxysuccinimide (18 mg) were added and the mixture was stirred for 5 h at room temperature. To the resulting reaction mixture, N-(5-aminopentyl)biotinamide, trifluoroacetic acid salt (80 mg) and $N(Pr-i)_2Et$ (0.05 mL) were added and the mixture was stirred at room temperature for 6 h. The solution was concentrated to about 3 mL and then diluted with MeOH (10 mL). To the solution, $K_2CO_3$ (300 mg) in water (10 mL) was added and stirred at room temperature for 3 h under $N_2$ in the dark. The mixture was poured into saturated brine (100 mL) and acidified with AcOH to pH 2. The acidified solution was extracted with EtOAc and the EtOAc layer washed with saturated brine and dried over anhydrous $Na_2SO_4$. The EtOAc extract was concentrated in vacuo and purified on a silica gel column using 10:1 $CHCl_3$/MeOH and 5:1 $CHCl_3$/MeOH as eluents to give compound 31 (30 mg).

Compound 31

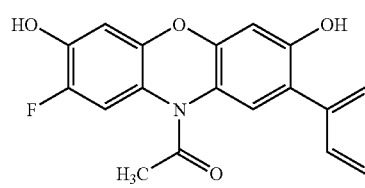 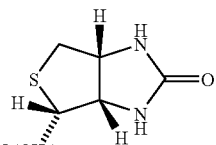

Example 33

Detection of H$_2$O$_2$ in the Presence of HRP in a Solution Assay

Amplex Red (Molecular Probes, Inc. A-12222) and Compound 4 were resuspended to 10 mM in dry DMSO. H$_2$O$_2$ was serially diluted two-fold across six rows of a 96-well microplate in 50 μl of 50 mM Tris, pH 7.5. 50 μl of 100 μM Amplex Red+2 Units/ml HRP or 50 μl of 100 μM Compound 4+2 Units/ml HRP were added to all wells and incubated at room temperature (~25° C.) for twenty minutes. The resulting fluorescence intensity was measured on a Victor$^2$ microplate reader (Wallac), 1 read/well for 0.2 sec each at 10000V gain, excitation 535+/−17.5 nm, emission 590+/−17.5 nm.

Initially the fluorescence intensity of both dyes is relatively stable in the presence of high concentrations of H$_2$O$_2$, but after twenty minutes of incubation, there is a biphasic mode to the dilution series, whereby the fluorescence has a peak at ~40 μM H$_2$O$_2$, then quickly drops at 80-160 μM H$_2$O$_2$ rising slowly at higher concentrations. See, FIG. 1

Example 34

Cyclooxygenase-2 Assay

Amplex Red (Molecular Probes, Inc. A-12222) and Compound 4 were resuspended to 10 mM in dry DMSO. Recombinant human cyclooxygenase-2 (COX-2, from Cayman Chemical) was serially diluted (in triplicate for each dye) two-fold in a 96-well microplate in 50 μl of 100 mM Tris, pH 8.0. 10 μl of 20 μM hemin (a COX-2 cofactor) in 100 mM Tris, pH 8.0 was added to all wells. After a five minute incubation at room temperature to allow the hemin to interact with the COX-2 enzyme, 40 μl of either 125 μM Amplex Red+250 μM arachidonic acid or 125 μM Compound 4+250 μM arachidonic acid in 100 mM Tris, pH 8.0 was added to all wells. The final reagent concentrations in the wells was zero to 50 Units/ml COX-2, 2 μM hemin, 100 μM arachidonic acid, and 50 μM Amplex Red reagent or Compound 4 in 100 μl of 100 mM Tris, pH 8.0.

The resulting reactions were incubated at 37° C. in the dark for thirty minutes. At that point, the resulting fluorescence was measured on a PerSeptive Biosystems CytoFluor 4000 microtiter plate reader (Framingham, Mass.). The excitation filter was 530 nm (+/−12.5 nm) and the emission filter 590 nm (+/−17.5 nm), with a gain setting of 40.

As FIG. 2 shows, both dye reagents are oxidized to their fluorescent forms by COX-2. The dynamic range and sensitivity of both dyes is similar with Compound 4 demonstrating a greater fluorescent intensity signal. Error bars in the graph are one standard deviation from the mean of three measurements. See, FIG. 2

Example 35

Hemoglobin Assay

Amplex Red (Molecular Probes Inc. A-12222) and Compound 4 were each resuspended to 10 mM in dry DMSO. Bovine hemoglobin (Sigma, catalog #H-2500) was serially diluted (in triplicate for each dye) two-fold in a 96-well microplate in 50 μl of 50 mM Tris, pH 7.5. 50 μl of either 100 μM Amplex Red+100 μM H$_2$O$_2$ or 100 μM Compound 4+100 μM H$_2$O$_2$ in 50 mM Tris, pH 7.5 was added to all wells. The final reagent concentrations in the wells was zero to 2000 ng/ml bovine hemoglobin, 50 μM H$_2$O$_2$, and 50 μM Amplex Red or Compound 4 in 100 μl of 100 mM Tris, pH 7.5.

The resulting reactions were incubated at 37° C. in the dark for thirty minutes. At that point, the resulting fluorescence was measured on a PerSeptive Biosystems CytoFluor 4000 microtiter plate reader (Framingham, Mass.). The excitation filter was 530 nm (+/−12.5 nm) and the emission filter 590 nm (+/−17.5 nm), with a gain setting of 40.

As the FIG. 3 shows, both dye reagents are oxidized to their fluorescent forms by bovine hemoglobin. The dynamic range and sensitivity of both dyes is similar, although Compound 4 is brighter. Error bars in the graph are one standard deviation from the mean of three measurements. See, FIG. 3

Example 36

Glycerol Assay

Amplex Red (Molecular Probes Inc. A-12222) and Compound 4 were each resuspended to 10 mM in dry DMSO. Glycerol (Sigma # G-7893) was serially diluted (in triplicate for each dye) two-fold in a 96-well microplate in 50 μl of 50 mM Tris, pH 7.5. 50 μl of either 100 μM Amplex Red+2 Unit/ml HRP+2 U/ml Glycerokinase (Sigma # G-0774)+2 U/ml Glycerol 3-phosphate oxidase (Sigma # G-4388)+1 mM ATP or 100 μM Compound 4+2 Unit/ml HRP+2 U/ml Glycerokinase (Sigma # G-0774)+2 U/ml Glycerol 1-phosphate oxidase (Sigma # G-4388)+1 mM ATP in 50 mM Tris, pH 7.5 was added to all wells. The final reagent concentrations in the wells was zero to 100 μM glycerol, 1 Unit/ml HRP+1 U/ml Glycerokinase+1 U/ml Glycerol 1-phosphate oxidase+0.5 mM ATP and either 50 μM Amplex Red or Compound 4 in 100 μl of 50 mM Tris, pH 7.5.

The resulting reactions were incubated at 37° C. in the dark for ten minutes. At that point, the resulting fluorescence was measured on a PerSeptive Biosystems CytoFluor 4000 microtiter plate reader (Framingham, Mass.). The excitation filter was 530 nm (+/−12.5 nm) and the emission filter 590 nm (+/−17.5 nm), with a gain setting of 35.

As FIG. 4 shows, both dye reagents are oxidized to their fluorescent forms by the action of HRP and H$_2$O$_2$ (H$_2$O$_2$ generated by the coupled-enzyme cascade). The dynamic range and sensitivity of both dyes is similar, although Compound 4 is brighter and hence a broader signal window. Error bars in the graph are one standard deviation from the mean of three measurements. See, FIG. 4

Example 37

Synthesis of Compound 32

To a 0.05 M solution of 2,7-difluororesorufin (Compound 2) in trifluoroacetic acid is added 15 equivalents of urea hydrogen peroxide addition compound (percarbamide) at room temperature. The resulting solution is stirred for 10 hours, or until TLC indicates reaction completion; on analytical TLC the resazurin Compound 32 has about ½ the R$_f$ of the starting resorufin in chloroform/methanol mixtures. The volatiles are removed in vacuo, and the residue is diluted with water and extracted with ethyl acetate (2×). The extract is dried over sodium sulfate, filtered, and concentrated in vacuo to yield Compound 32 as a red solid. This solid can be purified further by flash chromatography on medium silica gel using increasing amounts (up to 5%) of methanol in chloroform. Combine pure product fractions and concentrate in vacuo.

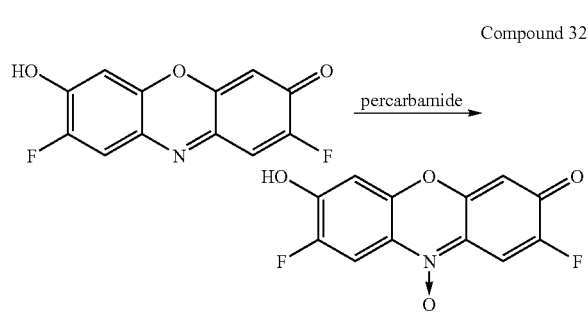

Example 38

C-Reactive Protein ELISA

Amplex Red (Molecular Probes Inc. A-12222) and Compound 4 were each resuspended to 10 mM in dry DMSO. C-reactive protein (Fitzgerald # 30-AC07) was serially diluted (in quadruplicate for each dye) three-fold in a 96-well ELISA microplate (Nunc # 449824) in 100 μl of 50 mM sodium phosphate, pH 7.4, 150 mM sodium chloride (PBS), and allowed to bind to solid-phase monoclonal mouse anti-human CRP (Fitzgerald # 10-C33) for 1 hour at 25° C. All wells were washed three times in 200 μl of PBS containing 0.1% Tween-20 (Aldrich # 274348) and 100 μl of PBS containing 50 ng/ml rabbit anti-human CRP (Calbiochem # 235752) was added to each well, and incubated at 25° C. for one hour. All wells were then washed three times in 200 μl of PBS containing 0.1% Tween-20, and 100 μl of 50 ng/mL goat anti-rabbit IgG-HRP conjugate (Molecular Probes # G-21234) was allowed to incubate at 25° C. in each well for 30 minutes. 100 μl of either 50 M Amplex Red+200 μM hydrogen peroxide (Aldrich # 323381) or 50 μM Compound 4+200 μM hydrogen peroxide (Aldrich # 323381) in 50 mM sodium phosphate, pH 7.4, 150 mM sodium chloride (PBS) was added to all wells. The final reagent concentration in the wells was zero to 6 ng C-reactive protein, 50 μM Amplex Red or Compound 4, 200 μM hydrogen peroxide in 100 μl of 50 mM sodium phosphate, pH 7.4, 150 mM sodium chloride.

The resulting reactions were incubated at 25° C. in a PerSeptive Biosystems CytoFluor 4000 microtiter plate reader (Framingham, Mass.). The excitation filter was 530 nm (+/−12.5 nm) and the emission filter 580 nm (+/−25 nm), with a gain setting of 35. Fluorescence was read every five minutes for up to one hour.

As FIG. 5 shows, both dye reagents are oxidized to their fluorescent forms by the action of goat anti-rabbit IgG-HRP conjugate and $H_2O_2$. The dynamic range and sensitivity of both dyes is similar, although Compound 4 is brighter and hence a broader signal window. Error bars in the graph are one standard deviation from the mean of four measurements. See, FIG. 5

Example 39 pH Tolerance Assay

Amplex Red (Molecular Probes Inc. A-12222) and Compound 4 were each resuspended to 10 mM in dry DMSO. Hydrogen peroxide (Aldrich # 323381) was serially diluted two-fold from 100 μM to zero in 100 μl of each of eight 100 mM buffers of different pH:

TABLE 4

| Buffer | PH |
|---|---|
| Sodium acetate (Sigma # S-8750) | 5.0 |
| MES (Sigma # M-3671) | 6.0 |
| MES (Sigma # M-3671) | 6.5 |
| MOPS (Sigma # M-1254) | 7.0 |
| MOPS (Sigma # M-1254) | 7.5 |
| Tris (Aldrich # 252859) | 8.5 |
| Borate (Sigma # S-9640) | 9.5 |
| CAPS (Aldrich # 163767) | 10.0 |

To each well, 100 μl of either 0.2 U/mL horseradish peroxidase (Sigma # P-8250)+100 μM Amplex Red (Molecular Probes Inc. A-12222) or 100 μM Compound 4 was added to begin the reaction.

The resulting reactions were incubated at 25° C. in a PerSeptive Biosystems CytoFluor 4000 microtiter plate reader (Framingham, Mass.). The excitation filter was 530 nm (+/−12.5 nm) and the emission filter 580 nm (+/−25 nm), with a gain setting of 35. Fluorescence was read every five minutes for up to thirty minutes.

Figure 6:
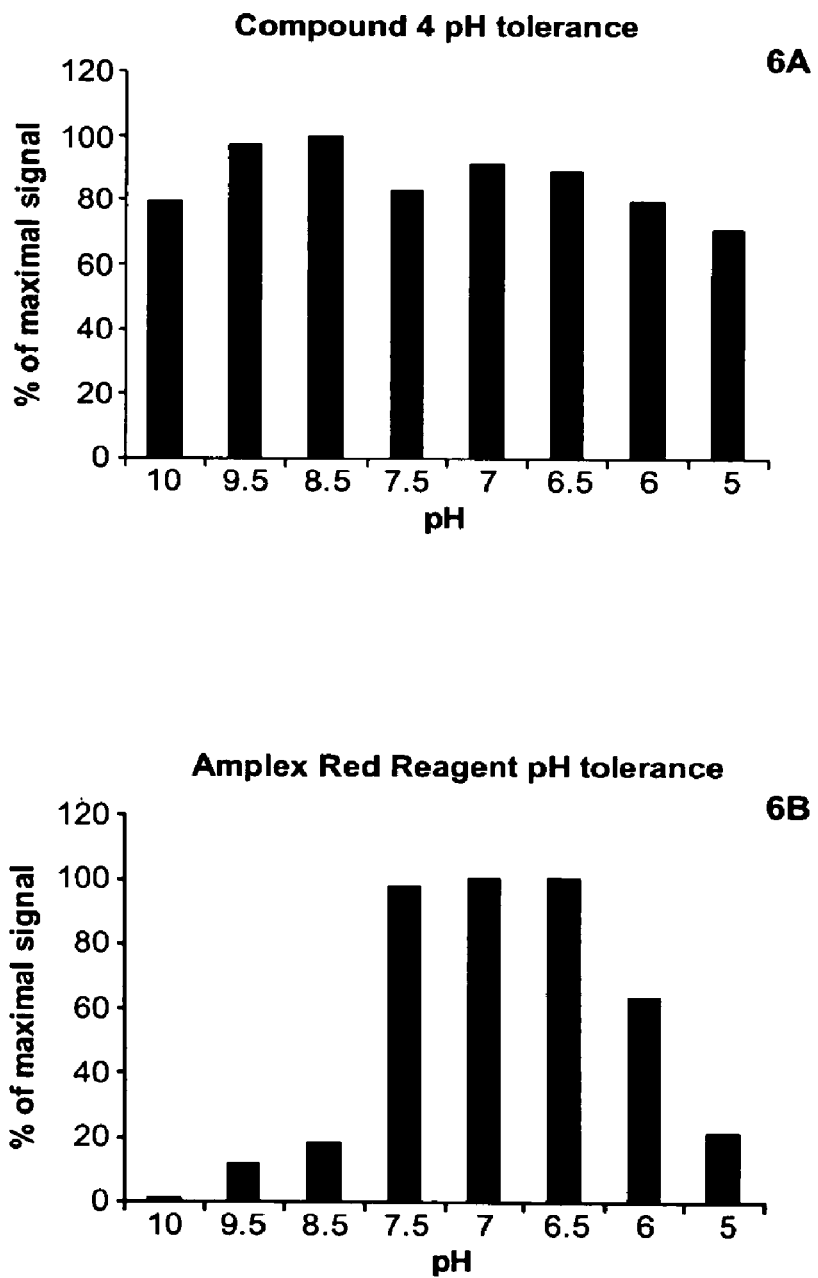
FIG. 6: is a graph showing the pH tolerance of Amplex Red reagent (6A) compared to the pH tolerance of Compound 4 (6B).

As the FIG. 6 shows, both dye reagents are oxidized to their fluorescent forms by peroxidase and $H_2O_2$. The sensitivity of both dyes is similar, but Compound 4 retains full fluorescence from pH 5 to 10 while Amplex Red has full fluorescence only from pH 6.5 to 7.5. See, FIG. 6

Example 40

Comparing Detection of LPS-Induced COX-2 Activity with Amplex Red Reagent and Compound 4

Two 100 mm plates of RAW 264.7 mouse macrophage cells (ATCC # TIB-71) were grown overnight to medium density in DMEM+10% FBS. The following morning the old media was removed and replaced with 12 ml fresh, warm, DMEM+10% FBS. To one plate, 12 μl of 100 μg/ml lipopolysaccharide (LPS) from E. coli strain 055:B5 (Sigma, catalog #L2880) in water was added. To the other plate, 12 μl of water alone was added. Both plates were incubated for 8 hours, 37° C., 5% $CO_2$. The cells from each plate were gently resuspended into ice-cold 100 mM Tris, pH 7.5 to 4000 cells/μl (counted by hemocytometer). Both batches of cells were lysed with a probe sonicator for 40 seconds with a 30% duty cycle using power output of 3 on a scale of 1 to 10. 50 μl of the resulting cell lysates were added to a 96-well microplate. 10 μl of 100 mM Tris, pH 7.5, +/−50 μM DuP-697 (Cayman Chemical catalog #70645), a COX-2 specific inhibitor, was added to all wells. The plate was incubated at room temperature (~24° C.) for 10 minutes to allow the COX-2 inhibitor time to inhibit the enzyme. 40 μl of 200 μM arachidonic acid (Cayman Chemical catalog #90010) and 100 μM dye (either Amplex Red or Compound 4) in 100 mM Tris, pH 7.5 was then added to the wells.

The final reagent concentrations in the wells was 200,000 lysed cell equivalents, +/−5 μM DuP-697, 80 μM arachidonic acid, and 40 μM Amplex Red or Compound 4 in 100 μl of 100 mM Tris, pH 7.5.

The resulting reactions were incubated at 37° C. in the dark for twenty minutes. At that point, the resulting fluorescence was measured on a PerSeptive Biosystems CytoFluor 4000 microtiter plate reader (Framingham, Mass.). The excitation filter was 530 nm (+/−12.5 nm) and the emission filter 590 nm (+/−17.5 nm), with a gain setting of 50.

Figure 7:
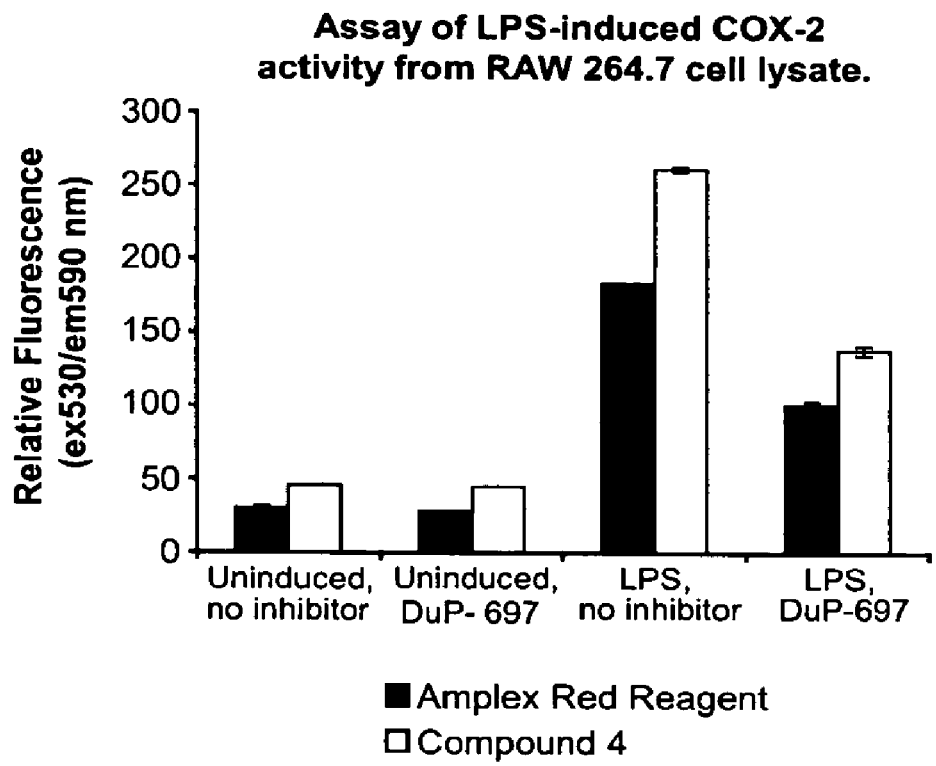
FIG. 7: is a graph showing the relative fluorescent signal generated by Amplex Red reagent compared to Compound 4 in an assay of LPS-induced COX-2 activity from RAW 264.7 cell lysate.

The graph of the resulting data demonstrates that both dyes can detect the presence of an oxidizing enzyme that is stimulated by the 8 hour LPS treatment. Approximately half of this oxidation can be inhibited by the COX-2-specific inhibitor DuP-697. Thus, both dyes can detect the presence of induced COX-2 in mouse macrophages. However, compound 4 demonstrates a stronger relative fluorescent signal, an improvement over the known Amplex red reagent. See, FIG. 7.

Example 41

Detection of Acid Phosphatase (Phytase) Activity with Amplex Red and Compound 4 at pH 5.5.

Phytases catalyze the sequential hydrolysis of phytate (myo-inositol hexakisphosphate; phytin; phytic acid) to less phosphorylated myo-inositol compounds and inorganic phosphate. This assay detects phytase activity on the basis of measurement of phosphate release from the substrate phytic acid. In a series of linked enzymatic reactions, phytase catalyzes the release of inorganic phosphate from phytic acid; maltose phosphorylase (EC 2.4.1.8) converts maltose (in the presence of $P_i$) to glucose 1-phosphate and glucose. Glucose oxidase (EC 1.1.3.4) converts the glucose to gluconolactone and $H_2O_2$. With horseradish peroxidase (HRP; EC 1.11.1.7) as a catalyst, the $H_2O_2$ reacts with the fluorogenic substrate (Amplex Red or Compound 4) to produce resorufin or difluororesorufin.

A dilution series of a commercial preparation of phytase (Natuphos® 10000L, BASF Wyandotte Corp, Wyandotte, Mich.; EC 3.1.3.8) was prepared in 0.1 M sodium acetate, pH 5.5. The enzyme dilutions were added to a CoStar 96-well round bottom plate in 50 µL aliquots. Mixtures containing 4 units/mL maltose phosphorylase, 2 units/mL glucose oxidase, 0.4 units/mL HRP, 2 mM phytic acid, 0.4 mM maltose, 0.1 M sodium acetate, pH 5.5, and 100 µM Amplex Red or 100 µM Compound 4 were prepared, and reactions were initiated by addition of 50 µL of reagent mixture to the enzyme dilution series. Reactions were done in triplicate, for 60 minutes at 37° C. Fluorescence was measured with a CytoFluor® Series 4000 Multi-Well Plate Reader (PerSeptive Biosystems, Framingham, Mass.), 530+/−12.5 nm excitation, 580+/−25 nm emission. The fluorescent signal was graphed as a function of phytase concentration expressed as international phytase units/mL (FTU/mL) (See, FIG. 8) and the Z-factor (Table 5) was calculated according to Zhang et al. (1999).

TABLE 5

Figure 8:
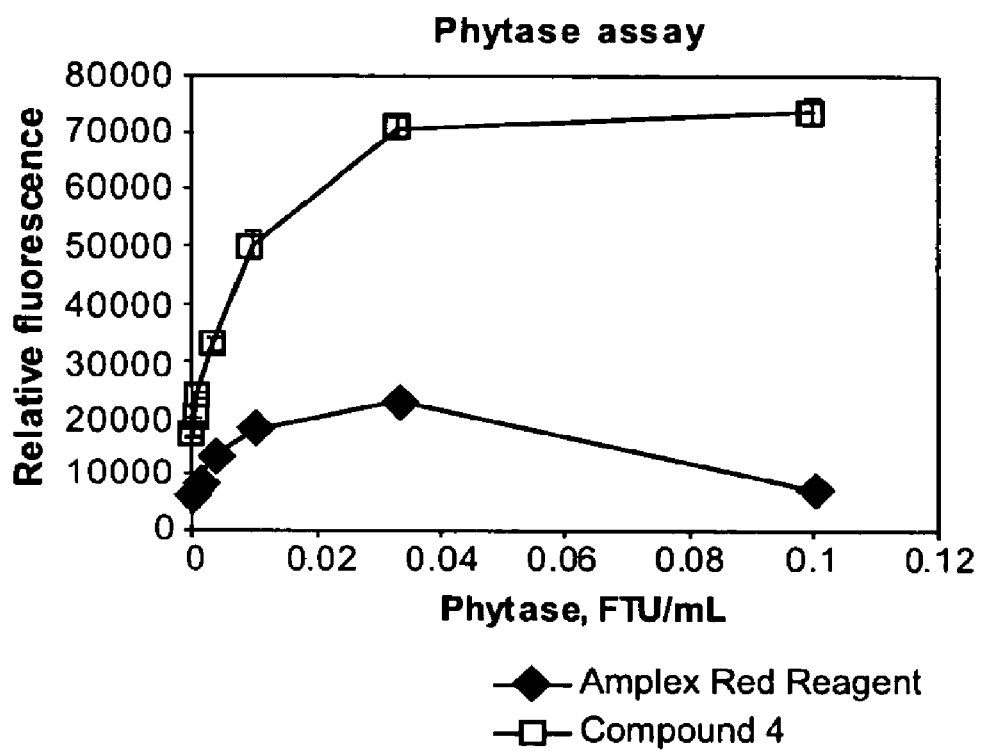
FIG. 8: is a graph showing relative fluorescence as a function of phytase concentration. Error bars are one standard deviation. See, Example 41

Z factor scores for data points shown in FIG. 8.

| Phytase, FTU/mL | Amplex Red Z-factor | Compound 4 Z-factor |
|---|---|---|
| 0.1 | −1.20 | 0.87 |
| 0.033 | 0.90 | 0.89 |
| 0.01 | 0.81 | 0.76 |
| 0.0033 | 0.13 | 0.76 |
| 0.001 | 0.30 | 0.64 |
| 0.00033 | −1.74 | 0.09 |

As shown graphically, the signal strength and dynamic range under these reaction conditions was significantly greater with Compound 4 as the reporting fluorogenic substrate. A Z-factor score of less than −1 or greater than 1 indicates an assay values that do not differ significantly or positively from the background value. With Compound 4 the lower limit of detection of phytase activity in the assayed sample is less than 0.00033 FTU/mL, and with Amplex Red the lower limit of detection is 0.001 FTU/mL.

Example 42

Detection of Horseradish Peroxidase Activity at Acidic pH: Comparison of Amplex Red and Compound 4

A dilution series of horseradish peroxidase (HRP; EC 1.11.1.7) was prepared in 0.1 M sodium acetate, pH 5.5. The enzyme dilutions were added to a CoStar 96-well round bottom plate in 50 µL aliquots. Mixtures containing 100 µM hydrogen peroxide ($H_2O_2$), 0.1 M sodium acetate, pH 5.5, and 100 µM Amplex Red or 100 µM Compound 4 were prepared, and reactions were initiated by addition of 50 µL of reagent mixture to the enzyme dilution series. Reactions were done in triplicate, for 60 minutes at 30° C. Fluorescence was measured with a CytoFluor® Series 4000 Multi-Well Plate Reader (PerSeptive Biosystems, Framingham, Mass.), 530+/−12.5 nm excitation, 580+/−25 nm emission. The fluorescent signal was graphed as a function of HRP concentration (See, FIG. 9) and the Z-factor (Table 6) was calculated according to Zhang et al. (1999).

TABLE 6

Figure 9:
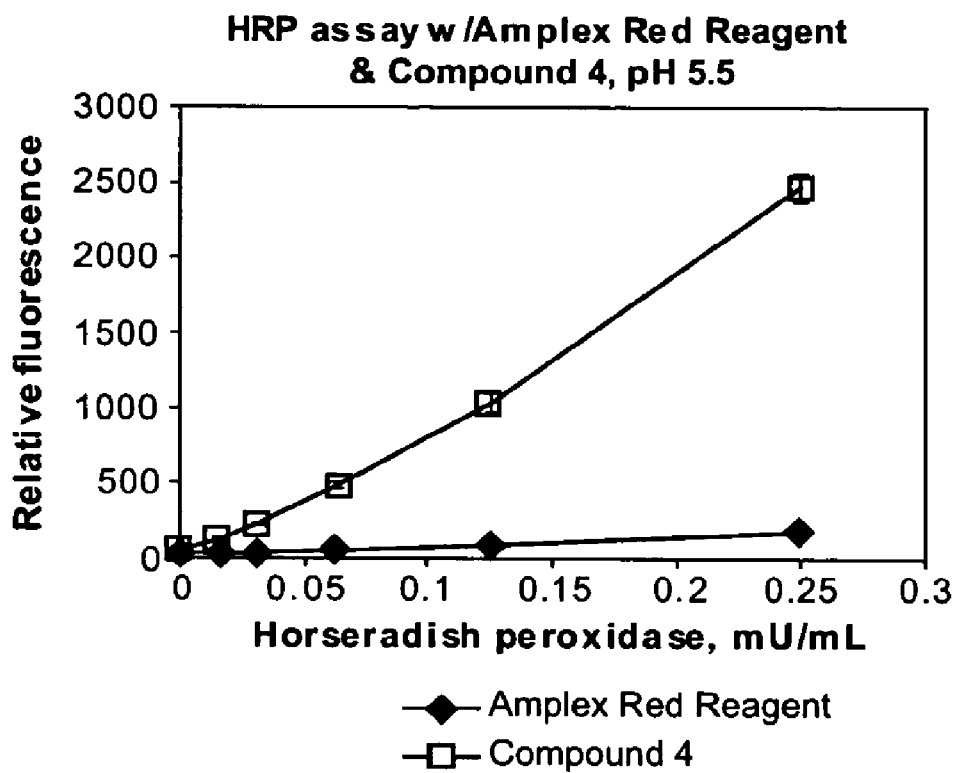
FIG. 9: is a graph showing relative fluorescence as a function of horseradish peroxidase concentration with 50 µM hydrogen peroxide (final assay concentration) at pH 5.5. Error bars are one standard deviation. See, Example 42.
Figure 10:
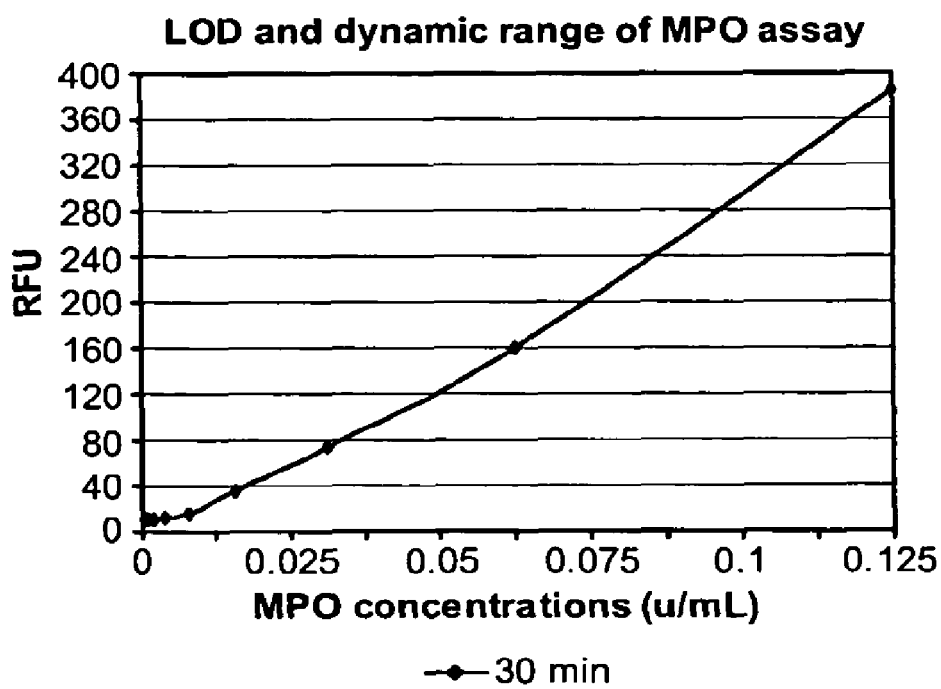
FIG. 10: is a graph showing the limit of detection and dynamic range for the detection of myeloperoxidase using Compound 4. See, Example 43.

Z factor scores for data points shown in FIG. 9.

| HRP, units/mL | Amplex Red Z-factor | Compound 4 Z-factor |
|---|---|---|
| 0.25 | 0.85 | 0.89 |
| 0.125 | 0.69 | 0.81 |
| 0.063 | 0.51 | 0.90 |
| 0.032 | 2.14 | 0.89 |
| 0.016 | 1.30 | 0.72 |

As shown graphically, the signal strength and dynamic range under these reaction conditions was significantly greater with Compound 4 as the reporting fluorogenic substrate. A Z-factor score of less than −1 or greater than 1 indicates an assay values that do not differ significantly or positively from the background value. With Compound 4 the lower limit of detection of HRP activity in the assayed sample is less than 0.016 enzyme units/mL, and with Amplex Red the lower limit of detection is 0.032 units/mL.

Example 43

Detection of Myeloperoxidase Using Compound 4

Myeloperoxidase (Sigma # M-6908) was diluted to 1 unit/mL using phosphate buffered saline (PBS, 50 mM sodium phosphate, pH 7.4, 150 mM sodium chloride). The solution was then serially diluted two fold using the same buffer. 50 µL of the preparations were added in a 96-well microplate (Nunc # 449824). 20 µL of 625 µM Compound 4 and 30 µl of 165 µM hydrogen peroxide (Aldrich # 323381) in PBS were added to all wells. The final reagent concentration in the wells was zero to 0.5 U/mL myeloperoxidase, 125 µM Compound 4 and 50 µM hydrogen peroxide in 100 µl of PBS.

The resulting reactions were incubated at 37° C. in a PerSeptive Biosystems CytoFluor 4000 microtiter plate reader (Framingham, Mass.). The excitation filter was 530 nm (+/−12.5 nm) and the emission filter 580 nm (+/−25 nm), with a gain setting of 35. Fluorescence was read every five minutes for up to 30 minutes.

As shown by the figure below, Compound 4 is oxidized to their fluorescent forms by the action of myeloperoxidase, chloride and $H_2O_2$. The assay can detect myeloperoxidase down to 0.0078 U/mL which is about 9.6 ng/mL. This limit of detection (LOD) is comparable with the results obtained from the most sensitive myeloperoxidase ELISA assay. The dynamic range of the assay is between 0.0078 U/mL and 0.125 U/mL. To the best of our knowledge this is the first time a fluorescent assay for myeloperoxidase has been presented. See, FIG. 10.

Example 44

Staining of Cells for Long Term Tracing of Living Cells Using Compound 30

Grow cells in an appropriate culture medium. Adherent cells can be grown on coverslips inside Petri dishes filled with culture medium. For example, a calf pulmonary arterial endothelium (CPAE) cell line is obtained from American Type Culture Collection Co., Rockville Md. The cells are maintained in a humidified atmosphere of 5% $CO_2$ in Dulbecco's modified Eagle's medium (DMEM) supplemented with 10% calf serum, 50 µg/mL gentamicin, 300 µg/mL L-glutamine and 10 mM HEPES pH 7.4. Cells are subcultured every 2-3 days by trypsinization using 0.05% trypsin and 0.02% EDTA in a calcium- and magnesium-free saline solution (Gibco BRL, Gaithersburg, Md.). To obtain well-spread single cells, cells are plated at a low density onto No. 1½ (18×18 mm) cover glasses in 100 mm culture dishes, and used 24-48 hours after plating.

Compound 30 is separately dissolved in DMSO to prepare a 1 mM to 10 mM dye stock solution. The stock solution is kept sealed in small aliquots, at −20° C. The stock solution is kept frozen at all times until use, and exposure to light is minimized. One aliquot of dye stock is taken from the freezer immediately before an experiment and thawed completely at room temperature. The labeling solution is then prepared by adding the dye stock solution to fresh culture medium in an amount sufficient to make final dye concentrations of 0.5-25 µM.

The optimal concentration of the dye for staining will vary depending upon the application. Testing at least a tenfold range of concentration is recommended. In general, long-term staining (more than about 3 days) or the use of rapidly dividing cells will require 5-25 µM dye. Less dye (0.5-5 µM) is needed for shorter experiments, such as viability assays. To maintain normal cellular physiology and reduce potential artifacts, the concentration of the dye should be kept as low as possible.

For cells in suspension, centrifuge the cells to pellet than and aspirate the supernatant. Resuspend the cells gently in prewarmed labeling solution. Incubate the cells for 15-45 minutes under growth conditions appropriate for the particular cell type. Centrifuge the cells. For adherent cells, when the cells have reached the desired confluence, remove the medium from the dish and add the prewarmed labeling solution. Incubate the cells for 15-45 minutes under growth conditions appropriate for the particular cell type.

Replace the labeling solution with fresh, prewarmed medium and incubate the cultures for another 30 minutes at 37° C. During this time, the chloromethyl group of Compound 30 will undergo modification or will be secreted from the cell. The chloromethyl group reacts with thiols, probably in a glutathione S-transferase reaction. Therefore Compound 30 is transformed into a cell-impermeant fluorescent dye-thioether adduct that can be fixed with aldehyde fixatives, permitting long-term sample storage. Excess unconjugated dye passively diffuses to the extracellular matrix.

The cells are attached to coverslips treated with BD-Cell-Tak (Beckton Dickenson; Franklin Lakes, N.J.) and then washed with PBS. The labeled cells are then observed using a Zeiss Axioplan epifluorescence microscope equipped with an appropriate filter set.

Example 45

Preparation of a Tyramine Conjugate

To a solution of Compound 28 (0.1 mmol) in anhydrous DMF (2 mL) is slowly added 1 mL DMF solution of tyramine (0.22 mmol). The resulted mixture is stirred at room temperature for 5-8 h until the dye is completely consumed. The reaction solution is concentrated in vacuo, and poured into ethyl acetate. The resulting precipitate is collected by filtration and washed with ethyl acetate. The crude material is further purified by HPLC to give the desired product.

Example 46

Cytotoxicity assay using Compound 32 (3H-phenoxazin-3-one, 2,8-difluoro, 7-hydroxy-, 10-oxide)

HeLa and HepG2 cells are obtained from the American Type Culture Collection. The cells are cultured in Dulbecco's modified Eagle medium (DMEM) supplemented with 10% fetal bovine serum (Invitrogen) until confluent. Cells are harvested by trypsinization and their density is assessed by hemocytometer. Cells are diluted in medium to a density of $1 \times 10^5$ cells per mL. 200 µL ($2 \times 10^4$ cells) of cell suspension is added to each well of a 96-well microplate. Cell samples are treated with various doses of cytotoxic test compounds (e.g. cisplatin 0.2-10 µg/mL) in serum-free medium for 2 hours during incubation in a humidified atmosphere at 37° C. and 5% $CO_2$. Compound 32 (10 µM) is then added to all cell samples including controls (no cytotoxic test compound added) followed by a further 2 hour incubation at 37° C. Fluorescence measurements on all samples is then performed at 37° C. using excitation at 530 nm and emission detection at 590 nm in a Victor$^2$ microplate reader (PerkinElmer Life Sciences). Cytotoxicity of the test compound is indicated by decreased fluorescence relative to the control samples.

Example 47

Preparation of a Phalloidin Dye-Conjugate

To aminophalloidin p-toluenesulfonate (3.5 mg, 4 µmol) and Compound 28 (6.0 mg, 5 µmol) in DMF is added N,N-diisopropylethylamine (2 µL, 11 µmol). The mixture is stirred at room temperature for 3 hours. To this is added 7 mL of diethyl ether. The solid is collected by centrifugation. The crude product is purified on SEPHADEX LH-20, eluting with water to give the pure phalloidin conjugate.

Example 48

Preparation of a Drug Dye-Conjugate

A fluorescent dopamine $D_2$ antagonist is prepared as follows: To 10 mg of N-(p-aminophenethyl)spiperone (Amlalky et al., FEBS LETT 176, 436 (1984)), and 10 µL N,N-diisopropylethylamine in 1 mL of DMF is added 15 mg of Compound 28. After 3 hours, the reaction mixture is poured into 5 mL ether. The precipitate is centrifuged, then purified by chromatography on silica gel using 10-30% methanol in chloroform.

Example 49

Preparation of Protein Dye-Conjugates

A series of dye conjugates of goat anti-mouse IgG, streptavidin and other proteins, including R-phycoerythrin (R-PE) are prepared by standard means (Haugland et al., METH. MOL. BIOL. 45, 205 (1995); Haugland, METH. MOL. BIOL. 45, 223 (1995); Haugland, METH. MOL. BIOL. 45, 235 (1995)) using Compound 28.

A solution of the desired protein is prepared at 10 mg/mL in 0.1 M sodium bicarbonate. The labeling reagents are dissolved in DMF at 10 mg/mL. Predetermined amounts of the labeling reagents are added to the protein solutions with stirring. A molar ratio of 10 equivalents of dye to 1 equivalent of protein is typical, though the optimal amount varies with the particular labeling reagent, the protein being labeled and the protein's concentration, and is determined empirically. The reaction mixture is incubated at room temperature for one hour, or on ice for several hours. The dye-protein conjugate is typically separated from free unreacted reagent by size-exclusion chromatography on BIO-RAD P-30 resin equilibrated with PBS. The initial, protein-containing colored band is collected and the degree of substitution is determined from the absorbance at the absorbance maximum of each fluorophore, using the extinction coefficient of the free fluorophore.

Example 50

Labeling and Use of a Wheat Germ Agglutinin Dye-Conjugate

Wheat germ agglutinin (100 mg, EY Laboratories) is dissolved in 5 mL NaHCO$_3$, pH 8.3, containing 9 mg N-acetylglucosamine. To this is added 9 mg of Compound 28. After 1 hour the solution is purified by gel filtration. A degree of substitution of 2-3 dyes per molecule is determined from the absorption at 633 nm.

A 1 mg/mL stock solution of the resulting wheat germ agglutinin (WGA) conjugate (Compound 28) is prepared in 0.1 M sodium bicarbonate ~pH 8. *Staphylococcus aureus* are cultured for 17 hours at 30° C. in TSB broth. Equal volumes of the TSB culture and a BSA solution (0.25% BSA+0.85% NaCl sterile filtered through 0.2 µM filter) are incubated at room temperature for 15 minutes. The BSA-bacterial suspension (200 µL) is centrifuged for 2 minutes at 350×g, capturing the bacteria on a filter membrane. The cells are resuspended in 90 µL of BSA solution and 10 µL of stain is added for 15 minutes. Following centrifugation, the bacteria are resuspended in BSA solution, and an aliquot is trapped between a slide and a glass coverslip.

The bacteria are observed on a Nikon Diaphot epi-fluorescence microscope. Images are acquired using the Star-1 cooled CCD camera and the software package supplied with the camera is used for data analysis. Two images are collected for each stain, each image having a 2 sec. exposure time. When used according to Sizemore et al. (U.S. Pat. No. 5,137, 810) the conjugate can distinguish between Gram positive and Gram negative bacteria.

Example 51

Detection of Lipase Activity

Compound 4 is resuspended to 10 mM in dry DMSO. In 50 µl of MOPS buffer, pH 7.2, glyceryl triacetate and Triton X-100 is serially diluted across a 96-well microplate. To this serial dilution, 50 µl of Compound 4, lipase (porcine pancreas, Sigma L-0382), glycerokinase (Sigma, G-0774), glycerol 1-phosphate oxidase (Sigma, G-4388), horseradish peroxidase (Sigma, P-8250), and ATP in MOPS buffer, pH 7.2 is added. The final concentration in the well is 25 µM Compound 4, 500 Units/ml lipase, 0.5 Unit/ml glycerokinase, 2 Units/ml glycerol 1-phosphate oxidase, 0.5 Units/ml horseradish peroxidase, 0.5 mM ATP, zero to 228 µM glyceryl triacetate, and zero to 0.5% Triton X-100 in 50 mM MOPS buffer, pH 7.2.

This mixture is reacted for sixty minutes in the dark at 37° C., then read in a fluorescence microplate reader. At that point, the resulting fluorescence is measured on a PerSeptive Biosystems CytoFluor 4000 microtiter plate reader (Framingham, Mass.). The excitation filter is 530 nm (+/− 12.5 nm) and the emission filter 590 nm (+/−17.5 nm), with a gain setting of 40.

This reaction results in oxidation of Compound 4, and subsequent detection by fluorescence. Compound 4 can be used to detect triglycerides using the assay described above.

The preceding examples can be repeated with similar success by substituting the specifically described fluorogenic compounds of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

It is understood that the examples and embodiments described herein are for illustrative purposes only and that various modifications or changes in light thereof will be suggested to persons skilled in the art and are to included within the spirit and purview of this application and are considered within the scope of the appended claims. All patents and patent applications cited herein are hereby incorporated by reference in their entirety for all purposes.

What is claimed is:

1. A method for determining the presence or absence of peroxide in a sample, wherein the method comprises:
   a) contacting the sample with a fluorogenic compound to prepare a labeled sample, wherein the fluorogenic compound has the formula;

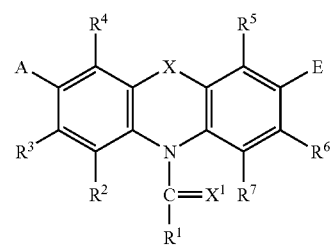

wherein
A is $OR^8$ or $NR^9R^{10}$;
E is $OR^8$ or $NR^9R^{10}$
wherein
$R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
$R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
$R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or
a member independently selected from
$R^9$ in combination with $R^{10}$;
$R^9$ in combination with $R^3$;
$R^9$ in combination with $R^6$;
$R^{10}$ in combination with $R^4$; and
$R^{10}$ combination with $R^5$
together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;
$R^1$ is substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$;
$X^1$ is oxygen or sulfur;
X is oxygen or sulfur;
$R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^5$ is hydrogen, halogen, substituted alkyl, unsubstituted alkyl, substituted alkoxy, unsubstituted alkoxy, substituted alkylthio, unsubstituted (alkylthio, substituted aryl, unsubstituted aryl, substituted heteroaryl, unsubstituted heteroaryl, sulfo, nitro, carboxyl, hydroxyl, or a reactive group;
$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or
a member independently selected from
$R^2$ combination with $R^3$; and
$R^6$ in combination with $R^7$
together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;
wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;
with the proviso that at least one member selected from $R^2$, $R^3$, $R^4$, $R^5$, $R^6$ and $R^7$ is fluorine;
b) incubating the labeled sample for a sufficient amount of time to prepare an incubated sample, wherein the peroxide reacts with the compound in the presence of a peroxidase to produce a fluorescent product;
c) illuminating the incubated sample with an appropriate wavelength to prepare an illuminated sample; and
d) observing the illuminated sample whereby the presence or absence of the peroxide in the sample is determined.

2. The method according to claim 1, wherein the peroxidase is horseradish peroxidase, myeloperoxidase or cyclooxygenase.

3. The method according to claim 1, wherein the peroxidase is covalently attached to a carrier molecule.

4. The method according to claim 3, wherein the carrier molecule is an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus.

5. The compound according to claim 3, wherein the carrier molecule is an antibody or fragment thereof, an avidin or streptavidin, a biotin, a blood component protein, a dextran, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

6. The method according to claim 1, wherein the peroxide is hydrogen peroxide.

7. The method according to claim 1, wherein the peroxide is a product formed by an enzymatic reaction.

8. The method according to claim 7, wherein the enzymatic reaction is the oxidation of a substrate using an oxidase.

9. The method according to claim 8, wherein the oxidase is selected from the group consisting of glutamate oxidase, amine oxidase, choline oxidase, cholesterol oxidase, galactose oxidase, xanthine oxidase, unease oxidase, pyruvate oxidase, glycerin-3-phosphate oxidase, acyl Co A oxidase, glycerol oxidase and glucose oxidase.

10. The method according to claim 8, wherein the enzymatic reaction and the reaction of the peroxide and the peroxidase with the compound are conducted simultaneously.

11. The method according to claim 10, wherein the peroxidase is horseradish peroxidase.

12. A method for determining the presence or absence of peroxide in a sample, wherein the method comprises:
a) generating peroxide from an enzymatic reaction wherein the enzymatic reaction is the oxidation of a substrate by an oxidase to prepare a peroxide containing sample;
b) contacting the peroxide containing sample with a fluorogenic compound to prepare a labeled sample, wherein the fluorogenic compound has the formula;

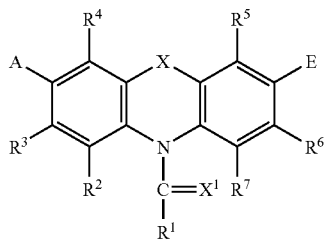

wherein
A is $OR^8$ or $NR^9R^{10}$;
E is $OR^8$ or $NR^9R^{10}$
wherein
$R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
$R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
$R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or
a member independently selected from
$R^9$ in combination with $R^{10}$;
$R^9$ in combination with $R^3$;
$R^9$ in combination with $R^6$;
$R^{10}$ in combination with $R^4$; and
$R^{10}$ combination with $R^5$
together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;
$R^1$ is substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$;
$X^1$ is oxygen or sulfur;
X is oxygen or sulfur;
$R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or a member independently selected from $R^2$ combination with $R^3$; and $R^6$ in combination with $R^7$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine;

c) incubating the labeled sample for a sufficient amount of time to prepare an incubated sample, wherein the peroxide reacts with the compound in the presence of a peroxidase to produce a fluorescent product;

d) illuminating the incubated sample with an appropriate wavelength to prepare an illuminated sample; and e) observing the illuminated sample whereby the presence or absence of peroxide in the sample is determined.

13. The method according to claim 12, wherein the peroxidase is horseradish peroxidase or myeloperoxidase.

14. The method according to claim 13, wherein the peroxide is hydrogen peroxide.

15. The method according to claim 12, wherein the peroxide is hydrogen peroxide.

16. The method according to claim 12, wherein the oxidase is selected from the group consisting of glutamate oxidase, amine oxidase, choline oxidase, cholesterol oxidase, galactose oxidase, xanthine oxidase, uricase oxidase, pyruvate oxidase, glycerin-3-phosphate oxidase, acyl Co A oxidase, glycerol oxidase and glucose oxidase.

17. The method according to claim 12, wherein the enzymatic reaction and the reaction of the hydrogen peroxide and the horseradish peroxidase with the compound are conducted simultaneously.

18. A method for determining the presence or absence of an analyte in a sample, wherein the method comprises:

a) contacting the sample with a peroxidase enzyme covalently attached to a carrier molecule to prepare a contacted sample, wherein the carrier molecule directly or indirectly associates with the analyte;

b) contacting the contacted sample with a fluorogenic compound to prepare a labeled sample, wherein the fluorogenic compound has the formula;

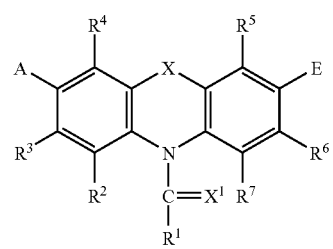

wherein

A is $OR^8$ or $NR^9R^{10}$;

E is $OR^8$ or $NR^9R^{10}$ wherein $R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or a member independently selected from $R^9$ in combination with $R^{10}$;

$R^9$ in combination with $R^3$;

$R^9$ in combination with $R^6$;

$R^{10}$ in combination with $R^4$; and $R^{10}$ combination with $R^5$ together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;

$R^1$ is substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$;

$X^1$ is oxygen or sulfur;

X is oxygen or sulfur;

$R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or a member independently selected from
$R^2$ combination with $R^3$; and
$R^6$ in combination with $R^7$
together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine;

c) incubating the labeled sample for a sufficient amount of time to prepare an incubated sample, wherein the peroxide reacts with the compound in the presence of a peroxidase to produce a fluorescent product;

d) illuminating the incubated sample with an appropriate wavelength to prepare an illuminated sample; and e) observing the illuminated sample whereby the presence or absence of the analyte in the sample is determined.

19. The method according to claim 18, wherein the peroxidase is horseradish peroxidase or myeloperoxidase.

20. The method according to claim 18, wherein the carrier molecule is an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus.

21. The method according to claim 18, wherein the carrier molecule is an antibody or fragment thereof, an avidin or streptavidin, a biotin, a blood component protein, a dextran, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

22. The method according to claim 18, wherein the carrier molecule specifically associates with the analyte.

23. The method according to claim 18, wherein the peroxidase is horseradish peroxidase and the carrier molecule is anti-IgG, anti-IgE or anti-IgA.

24. The method according to claim 18, wherein the peroxide is hydrogen peroxide.

25. A kit for the determination of peroxide in a sample, wherein the kit comprises:

a) a compound having the formula

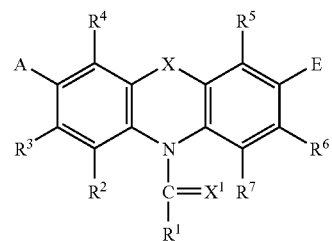

wherein
A is $OR^8$ or $NR^9R^{10}$;
E is $OR^8$ or $NR^9R^{10}$
wherein $R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or a member independently selected from
$R^9$ in combination with $R^{10}$;
$R^9$ in combination with $R^3$;
$R^9$ in combination with $R^6$;
$R^{10}$ in combination with $R^4$; and
$R^{10}$ combination with $R^5$ together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;

$R^1$ is substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$;

$X^1$ is oxygen or sulfur;

X is oxygen or sulfur;

$R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or a member independently selected from
$R^2$ combination with $R^3$; and
$R^6$ in combination with $R^7$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine; and b) an enzyme.

26. The kit according to claim 25, wherein the enzyme has oxidase or peroxidase activity.

27. The kit according to claim 25, further comprising a catalyst, a reaction buffer, an enzyme substrate, a peroxide, a stop solution, or a positive control.

28. The kit according to claim 27, wherein the positive control is an oxazine or a thiazine dye.

29. The kit according to claim 25, wherein the enxyme is horseradish peroxidase or myeloperoxidase.

30. The kit according to claim 27, wherein the peroxide is hydrogen peroxide.

31. A kit for determining the presence or absence of an analyte in a sample, wherein the kit comprises:

a) a peroxidase enzyme covalently attached to a carrier molecule; and b) a fluorogenic compound, wherein the compound has the formula

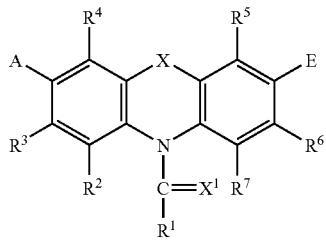

wherein
A is $OR^8$ or $NR^9R^{10}$;
E is $OR^8$ or $NR^9R^{10}$
wherein
  $R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
  $R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
  $R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or
  a member independently selected from
    $R^9$ in combination with $R^{10}$;
    $R^9$ in combination with $R^3$;
    $R^9$ in combination with $R^6$;
    $R^{10}$ in combination with $R^4$; and
    $R^{10}$ combination with $R^5$
  together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;
$R^1$ is substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$;
$X^1$ is oxygen or sulfur;
X is oxygen or sulfur;
$R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or
a member independently selected from
  $R^2$ combination with $R^3$; and
  $R^6$ in combination with $R^7$
together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;
wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine.

32. The kit according to claim 31, wherein the peroxidase is horseradish peroxidase.

33. The kit according to claim 31, wherein the carrier molecule is an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus.

34. The kit according to claim 31, wherein the carrier molecule is an antibody or fragment thereof, an avidin or streptavidin, a biotin, a blood component protein, a dextran, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

35. The kit according to claim 31, wherein the carrier molecule specifically associates with the analyte.

36. The kit according to claim 31, wherein the peroxidase is horseradish peroxidase and the carrier molecule is anti-IgG, anti-IgE or anti-IgA.

37. A composition for the quantitative determination of peroxide in a sample, wherein the composition comprises;
  a) a sample comprising peroxidase; and
  b) a fluorogenic compound that reacts with the peroxidase in the presence of the peroxide to form a fluorescent oxazine or chromogenic thiazine product proportional to the amount of peroxide in the sample, wherein the fluorogenic compound has the formula wherein
  A is $OR^8$ or $NR^9R^{10}$;
  E is $OR^8$ or $NR^9R^{10}$
  wherein
    $R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
    $R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;
    $R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or
    a member independently selected from
      $R^9$ in combination with $R^{10}$;
      $R^9$ in combination with $R^3$;
      $R^9$ in combination with $R^6$;
      $R^{10}$ in combination with $R^4$; and
      $R^{10}$ combination with $R^5$
    together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;
  $R^1$ is substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, $OR^8$ or $NR^9R^{10}$;
  $X^1$ is oxygen or sulfur;
  X is oxygen or sulfur;
  $R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
  $R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
  $R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
  $R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
  $R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;
  $R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or
  a member independently selected from
    $R^2$ combination with $R^3$; and
    $R^6$ in combination with $R^7$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine.

38. The composition according to claim 37, wherein the peroxidase is horseradish peroxidase or myeloperoxidase.

39. The composition according to claim 37, further comprising an enzymatic peroxide producing system in an amount sufficient to produce hydrogen peroxide.

40. The composition according to claim 39, wherein the enzymatic peroxide producing system comprises an oxidase enzyme.

41. The composition according to claim 40, wherein the oxidase enzyme is glutamate oxidase, amine oxidase, choline oxidase, cholesterol oxidase, galactose oxidase, xanthine oxidase, uricase oxidase, pyruvate oxidase, glycerin-3-phosphate oxidase, acyl Co A oxidase, glycerol oxidase or glucose oxidase.

42. A method for detecting metabolic activity in cells in a sample, wherein the method comprises:

a) contacting the sample with a compound to prepare a labeled sample, wherein the compound has the formula;

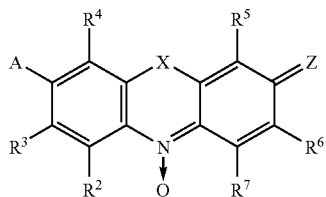

wherein
A is $OR^8$ or $NR^9R^{10}$;
Z is O or $N^+R^9R^{10}$;
wherein
$R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or a member independently selected from
$R^9$ in combination with $R^{10}$;
$R^9$ in combination with $R^3$;
$R^9$ in combination with $R^6$;
$R^{10}$ in combination with $R^4$; and
$R^{10}$ combination with $R^5$ together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;

X is oxygen or sulfur; and $R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or a member independently selected from
$R^2$ combination with $R^3$; and
$R^6$ in combination with $R^7$
together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine;

b) incubating the labeled sample for a sufficient amount of time to prepare an incubated sample, wherein the compound is capable of entering cells and being reduced to produce a fluorescent product;

c) illuminating the incubated sample with an appropriate wavelength; and d) observing the illuminated sample whereby the metabolic activity is detected and the resulting signal is proportional to the number of viable cells present in the sample.

43. A method for staining a sample, wherein the method comprises:

a) contacting the sample with a compound to prepare a labeled sample, wherein the compound has the formula:

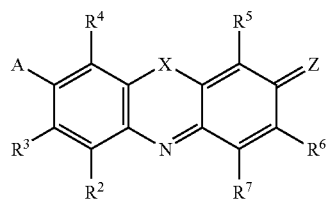

wherein
A is $OR^8$ or $NR^9R^{10}$;
Z is O or $N^+R^9R^{10}$
wherein
$R^8$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^9$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group;

$R^{10}$ is hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, unsubstituted alkoxy, or a reactive group; or a member independently selected from
$R^9$ in combination with $R^{10}$;
$R^9$ in combination with $R^3$;
$R^9$ in combination with $R^6$;
$R^{10}$ in combination with $R^4$; and
$R^{10}$ combination with $R^5$ together with the atoms to which they are joined, form a ring which is a 5-, 6- or 7-membered heterocycloalkyl, a substituted 5-, 6- or 7-membered heterocycloalkyl, a 5-, 6- or 7-membered heteroaryl, or a substituted 5-, 6- or 7-membered heteroaryl;

X is oxygen or sulfur;

$R^2$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^3$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^4$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^5$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^6$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group;

$R^7$ is hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, hydroxyl, or a reactive group; or a member independently selected from
  $R^2$ combination with $R^3$; and
  $R^6$ in combination with $R^7$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, a hydrazide, a succinimidyl ester, an imido ester, an isocyanate, an isothiocyanate, a maleimide, a phosphoramidite, a reactive platinum complex, a silyl halide, a sulfonyl halide, a thiol, an olefin, an acetylene, an alcohol, a phenol, an ether, an oxide, a halide, a ketone, an amide, a cyanate, an isocyanate, a thiocyanate, an isothiocyanate, a hydrazone, a diazo, a diazonium, a nitro, a nitrile, a sulfide, a disulfide, a sulfoxide, a sulfone, a sulfonic acid, a sulfinic acid, an acetal, a ketal, a sulfate, a sulfenic acid, an isonitrile, an amidine, an imide, an imidate, a nitrone, a hydroxylamine, an oxime, a hydroxamic acid, a thiohydroxamic acid, an allene, an ortho ester, a sulfite, an enamine, a ynamine, a urea, a pseudourea, a semicarbazide, a carbodiimide, a carbamate, an imine, an azo group, an azoxy group, or a nitroso group;

with the proviso that at least one member selected from $R^2$, $R^3$, $R^4$, $R^5$, $R^6$ and $R^7$ is fluorine;

b) incubating the labeled sample for a sufficient amount of time to prepare an incubated sample;

c) illuminating the incubated sample with an appropriate wavelength; and d) observing the illuminated sample whereby the sample is stained.

\* \* \* \* \*